(12) United States Patent
Sutliff et al.

(10) Patent No.: US 11,957,329 B2
(45) Date of Patent: Apr. 16, 2024

(54) SELF-RETAINING RETRACTOR

(71) Applicant: Simple Innovative Solutions, LLC, Mason, MI (US)

(72) Inventors: Jeffrey L. Sutliff, Mason, MI (US); Kris J. Cook, Dansville, MI (US)

(73) Assignee: Simple Innovative Solutions, LLC, Mason, MI (US)

( * ) Notice: Subject to any disclaimer, the term of this patent is extended or adjusted under 35 U.S.C. 154(b) by 150 days.

(21) Appl. No.: 17/567,836

(22) Filed: Jan. 3, 2022

(65) Prior Publication Data
US 2022/0117594 A1    Apr. 21, 2022

Related U.S. Application Data

(63) Continuation of application No. 16/841,658, filed on Apr. 6, 2020, now Pat. No. 11,213,286.

(51) Int. Cl.
*A61B 17/02* (2006.01)

(52) U.S. Cl.
CPC ...... *A61B 17/0206* (2013.01); *A61B 17/0218* (2013.01)

(58) Field of Classification Search
CPC . A61B 17/02; A61B 17/0293; A61B 17/0206; A61B 17/0218
See application file for complete search history.

(56) References Cited

U.S. PATENT DOCUMENTS

| | | | |
|---|---|---|---|
| 2,055,024 A | 9/1936 | Bittner | |
| 6,024,697 A | 2/2000 | Pisarik | |
| 6,322,500 B1 | 11/2001 | Sikora | |
| 6,808,493 B1 * | 10/2004 | Bookwalter | A61B 17/02 600/233 |
| 8,968,363 B2 | 3/2015 | Weiman et al. | |
| 10,278,686 B2 | 5/2019 | Baudouin et al. | |
| 11,213,286 B2 | 1/2022 | Sutliff et al. | |
| 2003/0004401 A1 | 1/2003 | Ball et al. | |
| 2006/0052672 A1 | 3/2006 | Landry et al. | |
| 2007/0110822 A1 | 5/2007 | Hinze | |
| 2011/0130793 A1 | 6/2011 | Woolley et al. | |
| 2013/0190575 A1 | 7/2013 | Mast et al. | |
| 2014/0257035 A1 * | 9/2014 | Blain | A61B 17/0218 600/104 |
| 2016/0317137 A1 * | 11/2016 | Predick | A61B 17/0206 |
| 2019/0021715 A1 * | 1/2019 | O'Connell | A61B 17/0293 |
| 2020/0253594 A1 * | 8/2020 | Wilson | A61B 17/7074 |
| 2020/0315604 A1 * | 10/2020 | Singla | A61B 17/0206 |
| 2020/0405281 A1 * | 12/2020 | Aksakal | A61B 17/0206 |

* cited by examiner

*Primary Examiner* — Ellen C Hammond
*Assistant Examiner* — Holly Joanna Lane
(74) *Attorney, Agent, or Firm* — Shay Glenn LLP

(57) ABSTRACT

Retractor assemblies and methods of using them to retract tissue. A retractor assembly as described herein may include first and second arms pivotally coupled and each arm formed of a plurality of stacked and separated plates, spaced to define a gap therebetween, providing strength while affording a reduction in weight of the retractor assembly. The retractor assembly may also include a ratcheting locking mechanism.

18 Claims, 24 Drawing Sheets

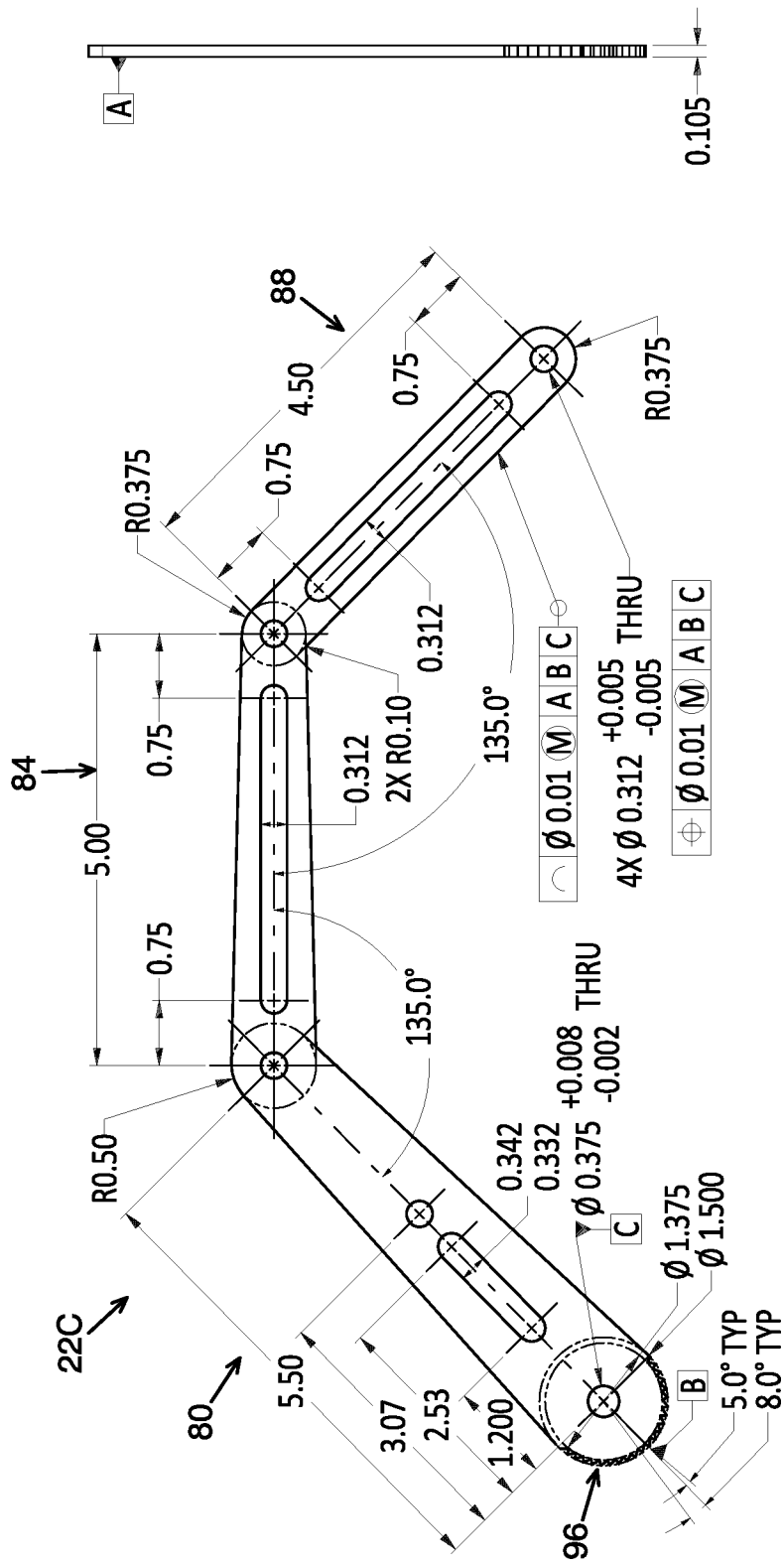

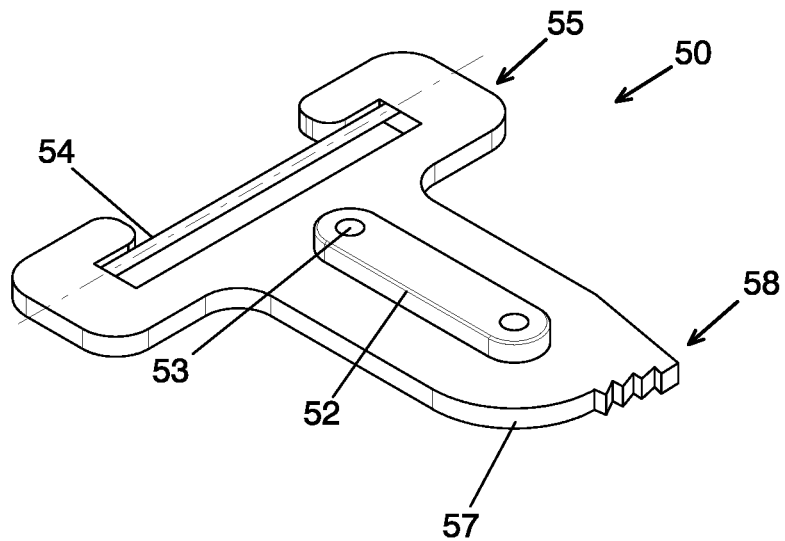
FIG. 14A
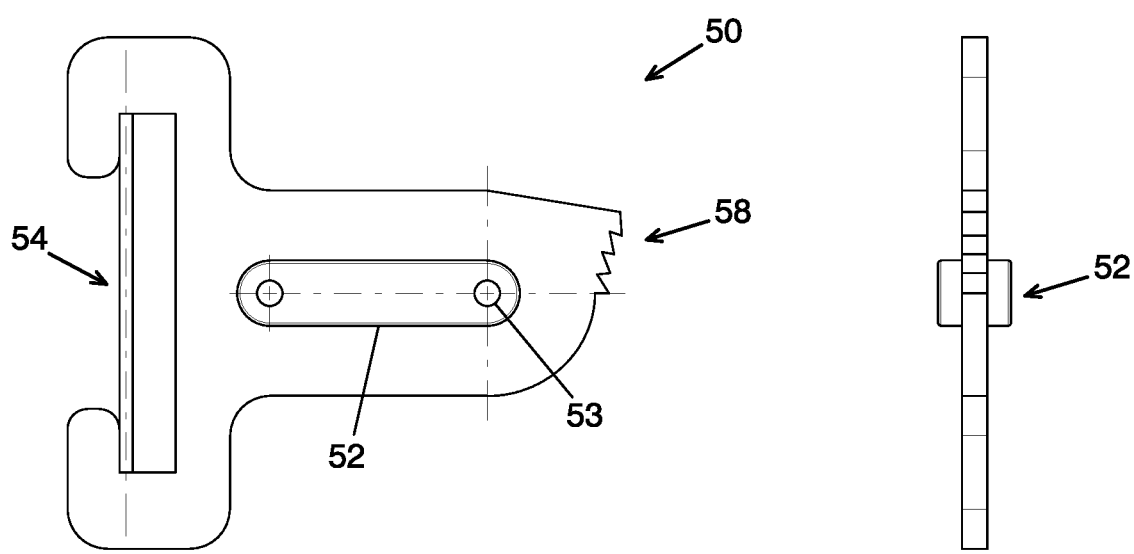
FIG. 14B     FIG. 14C

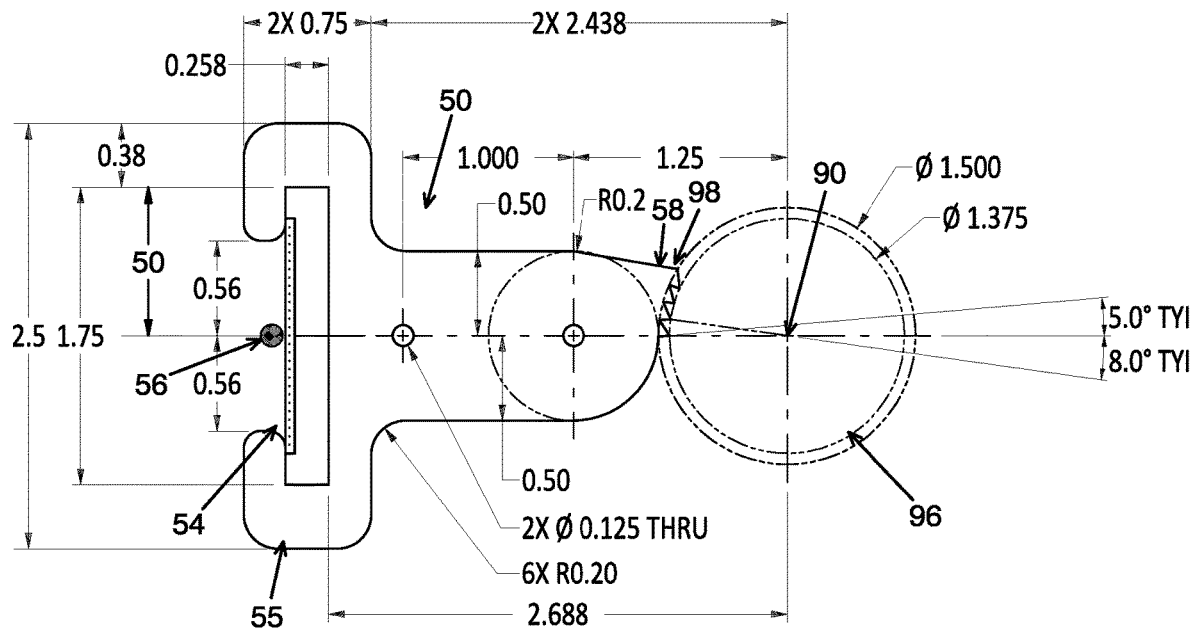
FIG. 16
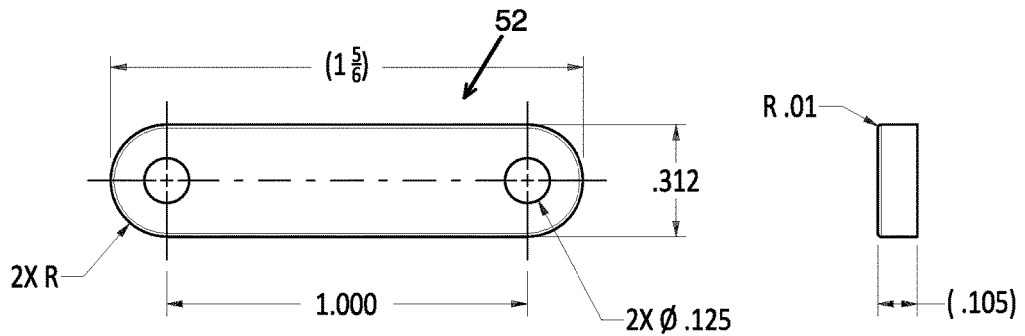
FIG. 17A  FIG. 17B

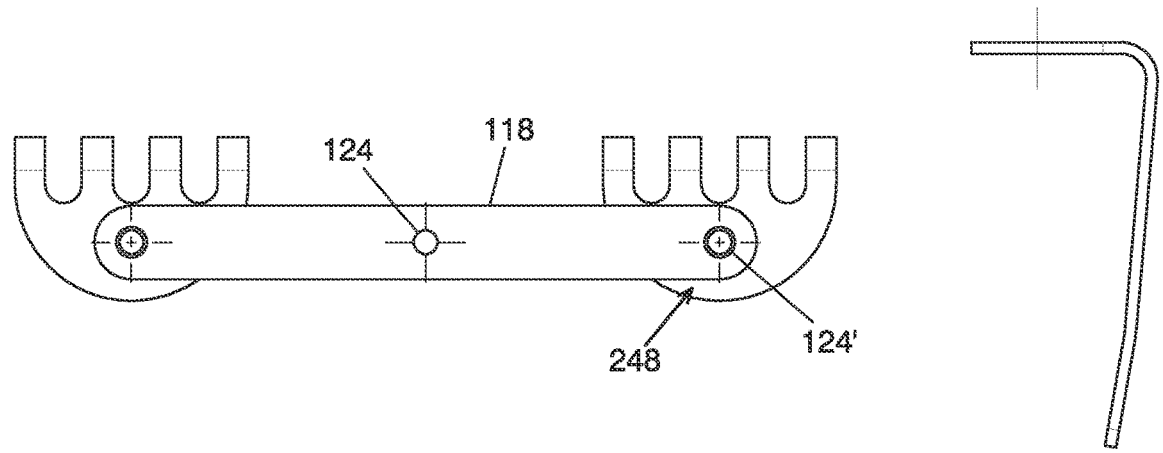
FIG. 18A  FIG. 18B
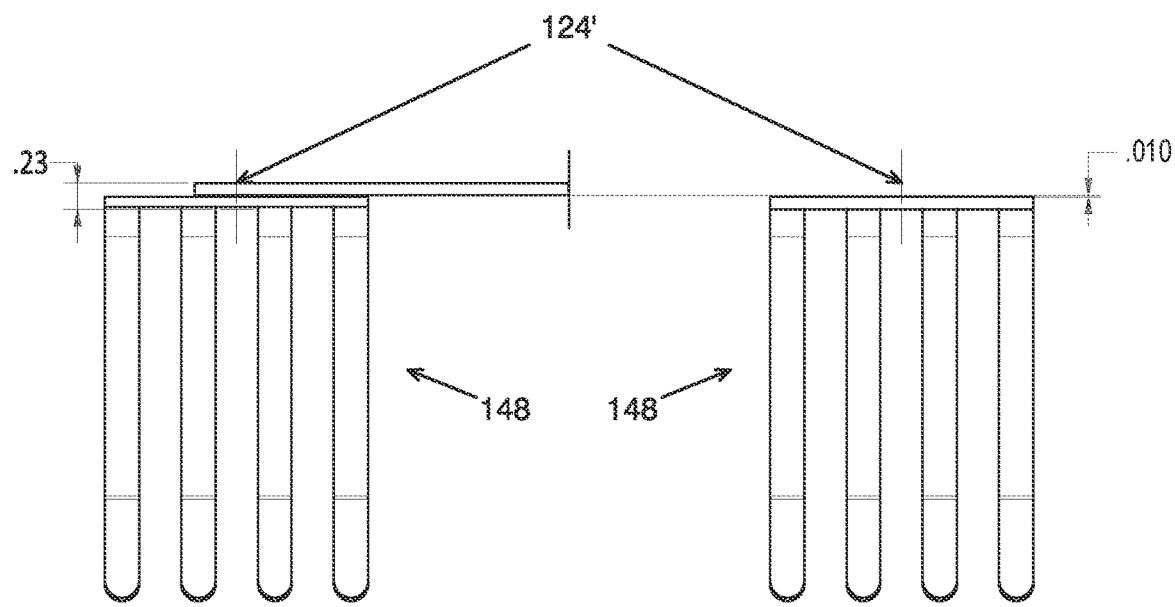
FIG. 18C

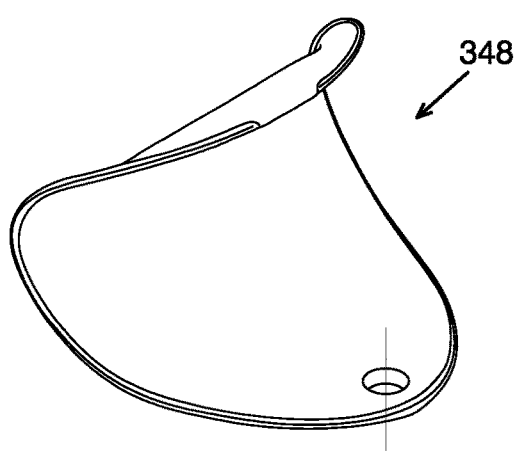
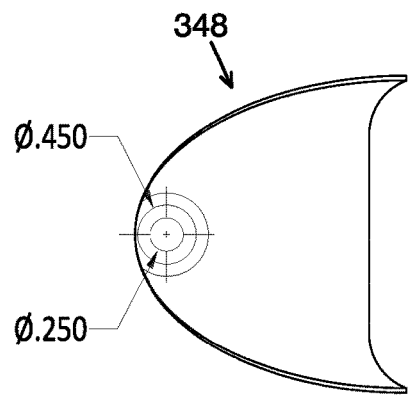
FIG. 19A　　　　　　　　FIG. 19B
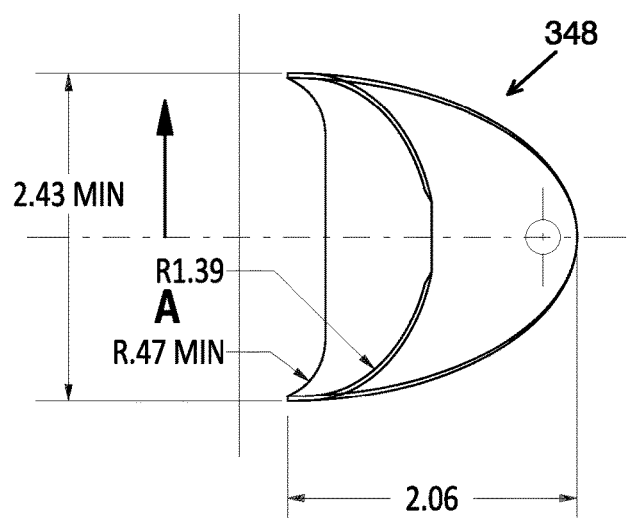
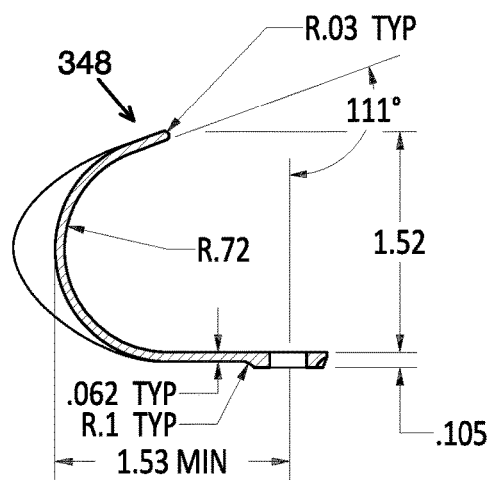
FIG. 19C　　　　　　　　FIG. 19D

SELF-RETAINING RETRACTOR

CROSS REFERENCE TO RELATED APPLICATIONS

This application is a continuation of U.S. patent application Ser. No. 16/841,658, filed Apr. 6, 2020, titled "SELF-RETAINING RETRACTOR," now U.S. Pat. No. 11,213,286, which is herein incorporated by reference in its entirety.

INCORPORATION BY REFERENCE

All publications and patent applications mentioned in this specification are herein incorporated by reference in their entirety to the same extent as if each individual publication or patent application was specifically and individually indicated to be incorporated by reference.

FIELD

Described herein are retractors (e.g., retractor apparatuses, including retractor devices and retractor assemblies). These retractors may be surgical tools used for surgery, including surgery upon live subjects, which may be humans or other animals, including mammalian animals, living or dead. For example, the apparatuses described herein may be used for surgery on a living human or non-human animal, and/or for recovery of organs from living or non-living humans or non-human animals.

BACKGROUND

Self-retaining retractors are widely used in the surgical field. Typically, retractors have a limited spread or opening ability and include at least one cross member to allow for adjustment. This limited range of motion and/or additional cross members can restrict, shrink, and/or block the visibility of the working field available to the medical staff to perform the respective procedure. Accordingly, it is desirable to have a retractor that can provide better visibility and a wider range of movement while additionally being simple to manipulate and lock into position.

SUMMARY OF THE DISCLOSURE

Described herein are improved retractor apparatuses (e.g., devices, systems, assemblies, etc.) and methods of using them. Retractors as described herein provide a number of advantageous elements, which may be used singly or in combination. A first improvement relates to retractor assemblies having multi-plate construction for each of a first arm and a second arm pivotally coupled together, which can lighten the overall retractor assembly while increasing its strength. The multi-plate construction may include two, three, four or more plates aligned to form a first arm or a second arm. The multi-plate construction includes a space (e.g., gap, slot, etc.) between each successive plate. The space permits insertion of the retractor assembly between other devices present within the surgical field. Alternatively, the presence of the space between successive plates of the arm may permit portions of a retractor blade or handle to insert itself therebetween, or may permit other devices present within the surgical field to be at least partially inserted therebetween.

The arms of the retractor assemblies may be configured to include one or more receiving wells, which may receive fasteners, which may couple one or more retractor blades of varying types to the retractor assemblies. Any of the one or more receiving wells may further be configured as a receiving slot, which may permit coupling of retractor blades or other devices or tools used during a surgical procedure. Whether coupled via a receiving well or a receiving slot, a retractor blade may be coupled rotatably or adjustably, and may further be capable of adjustment while still connected to the retractor assembly. In some variations, the coupling may be made via a quick connect pin or other quick releasing device.

Another improvement to retractor assemblies is improved locking mechanisms (e.g., ratcheting lock) for securing a first arm of the retractor assembly at a desired angle with respect to a second arm of the retractor assembly, where the first arm and the second arm are pivotally coupled to each other. The angle at which the first arm and the second arm are secured with respect to each other about the pivotal coupling, may be any angle, e.g., from about 5 degrees to about 180 degrees or may be any angles less than about 180 degrees. A variety of locking mechanisms may be used, including, but not limited to an eccentric cam lock mechanism, or a quick release locking mechanism, amongst others. It is desirable to open and secure the retractor assembly more easily during the surgical procedure, and permit adjustment during the course of the procedure. The locking mechanisms described herein permit locking at any selected angle within the range of operation of the retractor assembly. In some variations, the locking mechanism may be a self-locking mechanism such as the quick release mechanism (e.g., a quick release plate or plates) as described herein, or the like. The quick release locking mechanism may be disposed along each of the first and the second arm, near the pivot coupling point, and may include a pawl, which may be urged against a set of ratchet teeth of an opposite arm to permit opening and closing of the retractor assembly in a controllable, selective and self-locking (e.g., preventing closing, allowing opening) manner. The pawl may be urged against the set of ratchet teeth of the opposite arm by a bias (e.g., biasing strip or spring), which retains the pawl in engagement with the set of ratchet teeth. The pawl may be released from engagement by deflecting the bias against a restraining pin, to move the quick release mechanism away from the set of ratchet teeth, thereby disengaging the pawl.

Yet another improvement is provided by a retractor assembly having a first arm and a second arm, where each of the first and the second arms generally have a C-shape or conformation. The C-shape can provide a more open surgical field and better visibility to the surgical personnel. Each arm may include several sections connected, each at angle relative to the succeeding section, may have a curved shape or may have a multi-curved shape, providing the C-shape to the retractor assembly.

Accordingly, in a first aspect, a retractor assembly is provided including a first arm pivotally coupled to a second arm at a pivot; and a locking mechanism configured to lock the first arm and the second arm at a selected angle therebetween.

In some variations, the selected angle at which the first arm and second are locked relative to each other may be about 180 degrees or less. The locking mechanism may be configured to lock the first arm and the second arm at any angle from 5 degrees to 180 degrees.

In some variations, the first arm and the second arm may each include a first plate, a second plate, and a slot therebetween.

In some variations, the first arm and/or the second arm may further include one or more receiving wells. In some embodiments, at least one of the receiving wells of the first arm and/or the second arm may include an extended receiving slot. In some variations, the retractor assembly may further include a retractor blade coupled to a receiving well by a fastener. In some embodiments, the retractor blade may further include a sub-assembly including a self-positioning arm to which the retractor blade may be connected by a fastener, which may be rotatable, non-rotatable, or may be a quick releasing fastener.

In some variations, the locking mechanism may be a self-locking mechanism including a first quick release mechanism disposed along the first arm and a second quick release mechanism disposed along the second arm. In some variations, the first quick release mechanism may engage a first set of ratchet teeth disposed on a first end of the second arm and the second quick release mechanism may engage a second set of ratchet teeth disposed on a first end of the first arm. In some variations, the first quick release mechanism and the second quick release mechanism may be biased against the respective set of ratchet teeth by a bias.

In another aspect, a retractor assembly is provided including a first arm pivotally coupled to a second arm at a pivot, wherein each of the first arm and the second arm is a C-shaped arm. In some variations, the first arm and/or the second arm may include two or more sections, each disposed at an angle relative to each other, thereby forming the C-shaped arm.

In some variations, the angle between sections may be from about 110 degrees to about 145 degrees, and further wherein the angle is measured within a C-shape formed by the arm.

In some variations, the first arm and/or the second arm may further include one or more receiving wells. In some embodiments, at least one of the receiving wells of the first arm and/or the second arm may be an extended receiving slot. In some variations, the retractor assembly may further include a retractor blade coupled to a receiving well by a fastener.

In some variations, the retractor assembly may further include a self-locking ratcheting locking mechanism configured to lock the first arm and the second arm at a selected angle therebetween, preventing closing, while permitting opening of the two arms relative to each other.

In yet another aspect, a retractor assembly is provided including: a first, arm pivotally coupled to a second arm at a pivot, where the first arm and the second arm each include a first plate, a second plate, and a slot therebetween.

In some variations, the first arm and/or the second arm may further include one or more receiving wells. In some embodiments, at least one of the receiving wells of the first arm and/or the second arm may include an extended receiving slot. In some variations, the retractor assembly may further include a retractor blade coupled to a receiving well by a fastener. In some embodiments, the retractor blade may further include a sub-assembly including a self-positioning arm to which the retractor blade may be connected by a fastener, which may be rotatable, non-rotatable, or may be a quick releasing fastener.

In some variations, the retractor blade may be rotatably coupled to the receiving well, and is configured to insert at least a portion of the retractor blade within the slot.

In some variations, the retractor assembly may further include a self-locking, ratcheting locking mechanism configured to lock the first arm and the second arm at a selected angle therebetween.

For example, in general, a retractor device (e.g., retractor assembly) as described herein may include: a C-shaped first arm; a C-shaped second arm, wherein the first arm is pivotally connected to the second arm at a pivot; and a ratcheting lock configured to lock the first and second arms relative to each other to prevent them from reducing the angle between the arms until a release is activated, while allowing the angle between the first and second arms to be increased.

In some variations the retractor assembly includes: a C-shaped first arm the first arm comprising a first plate and a second plate that are separated from each other by a first spacing distance; a C-shaped second arm the second arm comprising a third plate and a fourth plate that are separated from each other by a second spacing distance, wherein the first arm is pivotally connected to the second arm at a pivot; a ratcheting lock configured to lock the first and second arms relative to each other to prevent them from pivoting to reducing the angle between the arms until a release is activated, while allowing them to be pivoted to increase angle between the first and second arms.

The C-shaped arms described herein are generally C-shaped, so as to form an opening to access the retracted tissue. The C-shape refers to an arm having a side (e.g., the side facing the opposite arm) that has a generally concave profile; the C-shaped arm may extend (top to bottom) through a general angle of curvature that is between 20 degrees and 270 degrees (e.g., measured from a midpoint of the circle approximately subtended by the curvature of the arm). For example, the C-shaped arm may be slightly curved (approximating a parenthesis), or very curved (approximating a textual C). The two arms may have different angles of curvature or the same angles of curvature. The angle of curvature may be smooth or segmented (as shown in the illustrated examples of the figures). For example, the first arm and/or the second arm may comprise two or more (e.g., 3, 4, 5, 6, etc.) sections, each disposed at an angle relative to each other, thereby forming the C-shaped arm.

As mentioned, the arms may each comprise a plurality of plates separated from each other by spacing distances. In some variations the plates each have a generally C-shape, and are stacked against each other with a gap between them. The gap may be between about 0.5 mm and about 2 cm (e.g., between 0.5 mm and about 1.5 cm, between about 0.5 mm and about 10 mm, between about 0.5 mm and about 7.5 mm, etc.).

The ratcheting lock may include one or more first quick release plates; for example, the ratcheting lock may include a first quick release plate disposed along the first arm and a second quick release plate disposed along the second arm. The quick release plate may include a pawl at one end and a bias (or a connection to a bias) at the other end; the pawl may include one or more teeth for engaging with a set of ratchet teeth on the opposite arm. In some variations the quick release plate includes a set of ratcheting teeth that engage with a pawl element on the opposite arm.

For example, a first quick release plate may engage with a first set of ratchet teeth disposed on a first end of the second arm and the second quick release plate engages a second set of ratchet teeth disposed on a first end of the first arm. In some variations only a single quick release plate (ratcheting connection) is used. The first quick release plate and the second quick release plate may be biased against the respective set of ratchet teeth by a bias (e.g., a Nitinol wire, band, etc., or a rubber/elastic band, wire, etc.). Any appropriate bias may be used, including a spring or the like.

The quick release plate may form the release that is configured to release the ratcheting lock to allow the first arm and the second arm to close, so that the angle between the first arm and the second arm is reduced. The release may be a protrusion (e.g., the head of the T-shaped quick release plate) that extends laterally from the gap in the plates of the arm from which the quick release plate is slidably coupled.

The first quick release plate may generally be slidably disposed between the plates forming the first arm and wherein the second quick release plate is slidably disposed between the plates forming the second arm.

Any of the retractors described herein may include one or more tissue engaging members (e.g., fingers, hands, retractor blades, retractor shields, etc.). The tissue engaging elements may generally couple to the distal ends (opposite of the pivot connecting the arms) of the arms, in a receiving well (e.g., through hole) in which it may be mounted (e.g., attached by a screw, post, etc., including pivotably mounted.

For example, a retractor assembly may include: a curved first arm the first arm comprising a first plate and a second plate that are separated from each other by a first spacing distance; a curved second arm the second arm comprising a third plate and a fourth plate that are separated from each other by a second spacing distance, wherein the first arm is pivotally connected to the second arm at a pivot, further wherein the curved first and second arms face each other so that the first arm forms a concave first curve and the second arm forms a concave second arm (this curve may be formed by generally straight segmented regions connected at an angle); a ratcheting lock configured to lock the first and second arms relative to each other to prevent them from pivoting to reducing the angle between the arms until a release is activated, while allowing them to be pivoted to increase angle between the first and second arms; and a first quick release plate slidably disposed between the first plate and the second plate, wherein the first quick release plate is biased against a set of ratchet teeth in the second arm, further wherein a portion of the first quick release plate forms the release.

Also described herein are methods of using the retractors described herein. For example, a method of retracting tissue may include: positioning a first arm of a retractor assembly against a first portion of a tissue; positioning a second arm of the retractor assembly against the second portion of the tissue; ratcheting the first arm relative to the second arm to retract the tissue so that the tissue is accessible between a C-shaped portion of the first arm and a C-shaped portion of the second arm, wherein a ratcheting lock in the retractor assembly prevents the angle between the first arm and the second arm from being reduced while permitting the angle to be increased by pivoting the first arm away from the second arm; and inserting one or more tools at least partially into a space formed between a first c-shaped plate and a second C-shaped plate forming the first arm.

Any of these methods may include releasing the ratcheting lock to allow the first arm to pivot closer to the second arm and reduce the angle between the first and second arms by sliding a first quick release plate between the first and second C-shaped plates of the first arm, removing a pawl on the first quick release plate from a set of ratchet teeth on the second arm. Releasing the ratcheting lock may comprise deflecting a bias on the quick release plate.

BRIEF DESCRIPTION OF THE DRAWINGS

A better understanding of the features and advantages of the methods and apparatuses described herein will be obtained by reference to the following detailed description that sets forth illustrative embodiments, and the accompanying drawings of which:

FIGS. 12A and 12B are graphical representations of a top perspective view and a side perspective view respectively of a plate of an arm of a self-retaining retractor according to some embodiments of the disclosure.

FIGS. 14A to 14C show examples of a perspective view, a top view and a side view of one variation of a first quick release mechanism (e.g., quick release plate) according to some embodiments of the disclosure.

FIG. 16 is a graphical representation of a portion of a quick release plate and elements of the ratchet of a plate of an arm of the retractor assembly according to some embodiments of the disclosure.

FIGS. 17A and 17B are graphical representations of a top and side view of a guide bar of the quick release plate according to some embodiments of the disclosure.

FIGS. 18A-18C are graphical representations of top and side views of retractor blades and attachment thereof according to some embodiments of the disclosure.

FIGS. 19A-19D are graphical representations of another retractor blade according to some embodiments of the disclosure.

DETAILED DESCRIPTION

Figure 1:
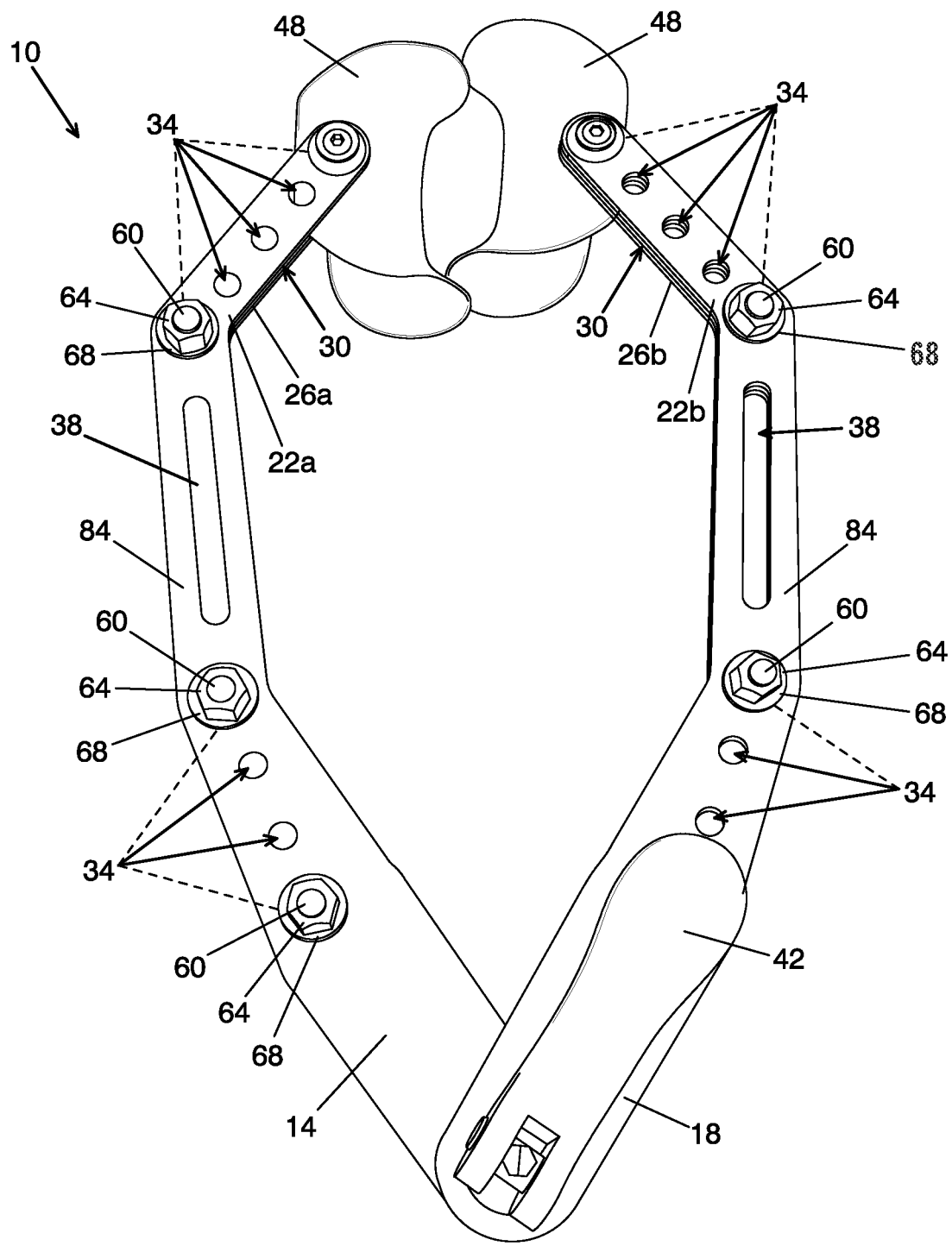
FIG. 1 is a photographic representation of a top perspective view of a self-retaining retractor in a first position according to some embodiments of the disclosure.

As used herein, the term "and/or," when used in a list of two or more items, means that any one of the listed items can be employed by itself, or any combination of two or more of the listed items can be employed. For example, if a composition is described as containing components A, B, and/or C, the composition can contain A alone; B alone; C alone; A and B in combination; A and C in combination; B and C in combination; or A, B, and C in combination.

As used herein, the term "about" means that amounts, sizes, formulations, parameters, and other quantities and characteristics are not and need not be exact, but may be approximate and/or larger or smaller, as desired, reflecting tolerances, conversion factors, rounding off, measurement error and the like, and other factors known to those of skill in the art. When the term "about" is used in describing a value or an end-point of a range, the disclosure should be understood to include the specific value or end-point referred to. Whether or not a numerical value or end-point of a range in the specification recites "about," the numerical value or end-point of a range is intended to include two embodiments: one modified by "about," and one not modified by "about." It will be further understood that the endpoints of each of the ranges are significant both in relation to the other endpoint, and independently of the other endpoint.

For purposes of this disclosure the term "coupled" (in all of its forms: couple, coupling, coupled, etc.) generally means the joining of two components (electrical or mechanical) directly or indirectly to one another. Such joining may be stationary in nature or movable in nature. Such joining may be achieved with the two components (electrical or mechanical) and any additional intermediate members being integrally formed as a single unitary body with one another or with the two components. Such, joining may be permanent in nature, or may be removable or releasable in nature, unless otherwise stated.

FIGS. 1-24, show a retractor assembly, generally denoted as a retractor assembly 10. Reference numbers are reiterated for similar elements throughout FIGS. 1-24. Retractor assembly 10 includes first and second arms 14, 18 pivotally coupled and each having at least a first plate 22a, 22b and a second plate 26a, 26b. While two plates are shown in the FIGS. 1-24, the retractor assembly 10 is not so limited and there may be 2, 3, 4 or more plates in retractor assembly 10, each separated by a slot 30 between each plate of the arm. The first and second plates 22a, 22b, 26a, 26b of each of the first and second arms 14, 18 are spaced to define the slot 30, that is, plate 22a overlays plate 26a of first arm 14 and plate 22b overlays plate 26b of the second arm 18, and slot 30 is formed between the respective plates of the first arm 14 and second arm 18. Use of a first plate and second plate (and possibly more) to construct arm 14, 18 permits the retractor to be lighter for its strength, due to the multiple plates. Additionally, the presence of slot(s) 30 in each arm permit insertion of the retractor assembly between other devices or other devices may be inserted in or through a slot. The retractor assembly 10 further comprises a plurality of receiving wells 34 defined by each of the first and second arms 14, 18. One or more of the receiving wells 34 may be a receiving slot 38. The retractor assembly 10 also includes a locking mechanism, which may be any of the locking mechanisms described herein, and their like. The locking mechanism, which may be any locking mechanism described herein or the like, of retractor assembly 10 can lock arm 14 and arm 18 at a selected angle relative to each other for optimized surgical field size. The locking mechanism may lock the first arm 14 and the second arm 18 at an angle relative to each other of about 5 degrees; about 10 degrees; about 25 degrees; about 45 degrees; about 60 degrees; about 75 degrees; about 90 degrees; about 135 degrees; about 145 degrees; about 170 degrees; about 180 degrees; or any angle therebetween. In some embodiments, the locking mechanism may permit locking the first arm 14 and the second arm 18 from about 10 degrees to about 180 degrees, about 15 degrees to about 180 degrees, about 30 degrees to about 180 degrees, about 60 degrees to about 180 degrees, about 75 to about 180 degrees, about 90 to about 180 degrees, about 110 degrees to about 180 degrees or any range selected therebetween, preventing further closing (while generally allowing further opening) of the retractor. In some embodiments, the locking mechanism may permit locating the first arm 14 and the second arm 18 at an angle that is 180 degrees or less.

Each receiving well 34 may be configured to receive a fastener 60. The fastener 60 may be secured by a plurality of bolts 64 and washers 68, a pressure fitting or a quick connect mechanism such as a pin. The bolts 64 and washer 68 may be used to space apart the first and second plates 22a, 26a of the first arm 14 and the first and second plates 22b, 26b of the second arm 18 to form a slot 30, e.g., a space between the first and the second plates of each arm 14, 18. The slot 30 extends the length of each of the first arm 14 and the second arm 18 and is configured to receive retractor blades 48 or other tools, such as, but not limited to other surgical tools or a camera. In some examples, the slot 30 may allow a handle 102 of a retractor blade 48 to be movable in various directions, e.g., adjusted to differing positions within a surgical field (See FIGS. 3 and 4). In some examples, the slot 30 may be spaced by washers (see FIG. 9). In other examples, the slot 30 may be spaced by tube expansion, rolling, and flaring to secure a ball within the tube. The slot 30 may be any width to allow various portions of the retractor blades 48 to move between the first and second plates 22a, 22b, 26a, 26b.

The retractor assembly 10 may have one or more, typically two or more retractor blades 48 attached to the first arm 14 and the second arm 18. The retractor blades 48 may each be any retractor blade described herein.

The first arm 14 and the second arm 18 each includes a first end 80, the midsection 84, and a second end 88. The first end 80 may be positioned at a predetermined angle relative to the midsection 84, and the midsection 84 may be positioned at a predetermined angle relative to the second end 88. In some examples, the predetermined angles may be within the range of about 110 degrees to about 160 degrees, about 110 degrees to about 150 degrees, about 110 to about 15 degrees, or about 130 degrees to about 145 degrees, measuring within the interior angle between the sections of the arm. In FIG. 12 A, this is illustrated for an exemplary angle of 135 degrees. In other examples, the predetermined angles may be within the range of about 145 degrees to about 160 degrees. The angles of the respective first end 80, midsection 84, second end 88 of the first arm and second arm may be modified to obtain a larger (e.g., more open) or a smaller (e.g., more restricted) incision site as desired for a particular application. The angles of the respective first end 80, midsection 84, second end 88 of the first arm and second arm may form a C-shaped surgical working region defined by the arms. A more open incision site can provide facilitated movements and speed a surgery. Alternatively, a smaller opening (smaller distance between retractor blades 48 of the first arm 14 and second arm 18 may permit surgical manipulations to be performed, reducing surgical recovery. It will be understood that the lengths and angles of the first end 80, the midsection 84, and the second end 88 may vary while maintaining the same proportion to allow for variation in size of the retractor assembly 10. For example, different retractor assemblies may be sized appropriately for adult human surgical procedures or for juvenile or perinatal human surgical procedures. Larger or smaller retractor assemblies may be produced for operability upon animals smaller or larger than humans. The angles may be the same or different, and it will be understood that there may be more than two angles formed by one of the first arm 14 and second arm 18 without departing from the scope of the present disclosure. Additionally, it will be understood that there may be more sections of the first arm 14 and the second arm 18 and the design is not limited to the three sections mentioned here. For example, the first and second arms 14, 18 may include four sections, five sections, six sections, etc. without departing from the scope of the present disclosure. In other examples, the first and second arms may be non-linear with one continuous section, e.g., the first arm and/or the second arm may be a curved or multi-curved shaped arm.

A retractor assembly 10, like any described herein, including the first and second arms 14, 18 and the retractor blades 48 (including 248, 348), may be made entirely of surgical grade steel or any other material, including metals or ceramics, that may be clinically acceptable. The slot 30 allows for the retractor assembly 10 to be lighter than other retractors of the same material while still being sturdy. Additionally, for ease of use, the retractor blades 48 and self-positioning arm 120, described below, may be operably coupled to the first and second arms 14, 18 and the receiving wells 34 by ball and socket connections to allow a wide range of movement of the retractor blades 48. In some examples, the fasteners 60 and bolts 64 may be replaced by press and/or quick connect fittings to allow easy removal and adjustment of the retractor assembly 10. This eliminates the possibility of loss of bolts 64 or washers 68 in a medical situation that could cause additional time loss. Fasteners 60 and bolts 64 may further include rotatable fasteners, including bolts, washers, press or quick connect fittings permitting rotation of the attachments (self-positioning arm 120, retractor blades 48 and the like) about the receiving well 34.

Figure 2:
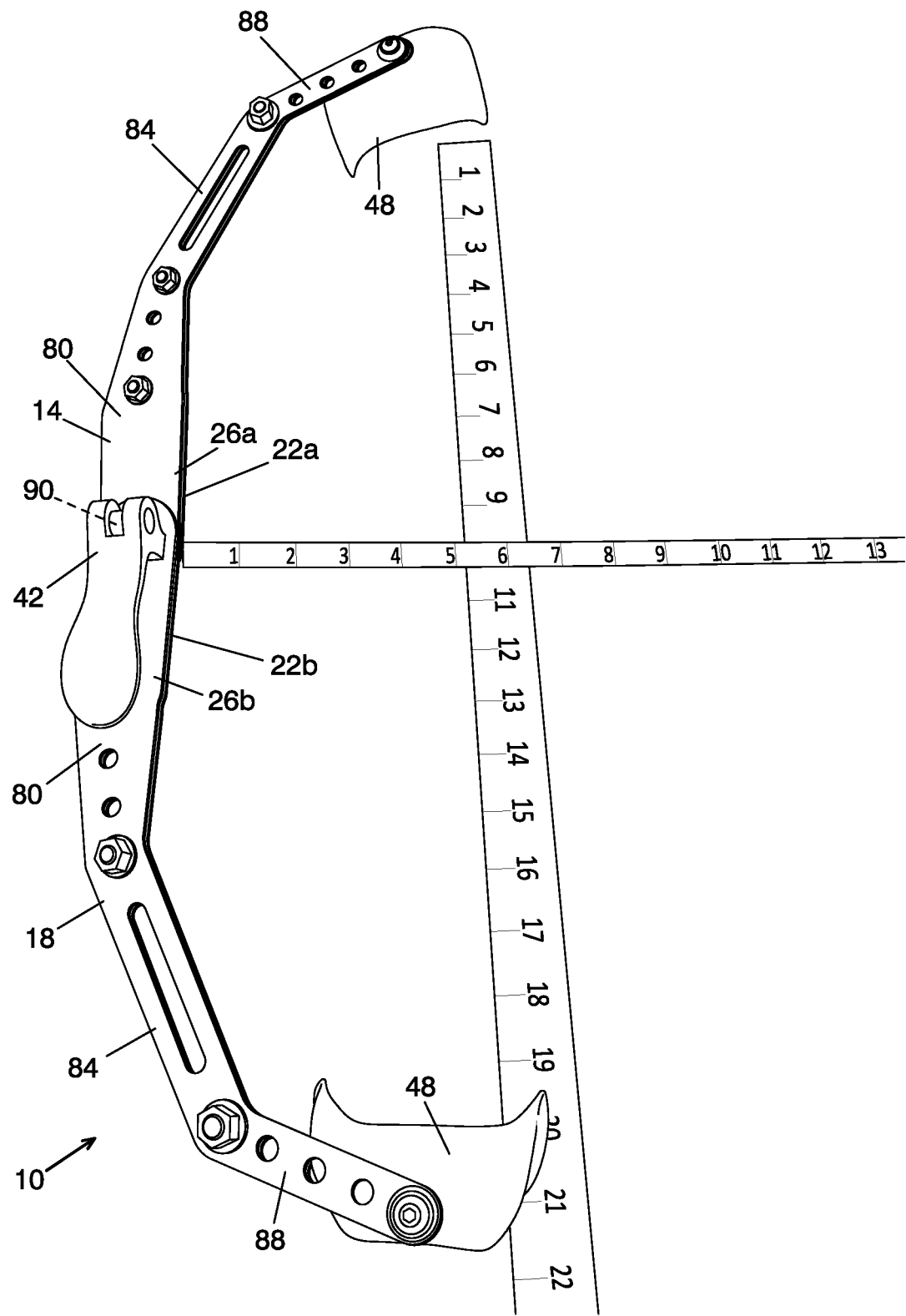
FIG. 2 is a photographic representation of a top view of the self-retaining retractor of FIG. 1 in a second position according to some embodiments of the disclosure.

Turning to specific exemplary retractor assemblies, in FIGS. 1-2, the retractor assembly 10 includes one embodiment of a locking mechanism, an eccentric quick-lock cam lever 42 configured to lock the first and second arms 14, 18 in a selected position. The operation of the retractor assemble may be understand by referring to FIG. 1. However, any of the retractor assemblies described herein may operate similarly, even if differing lock mechanisms and differently configured pivot regions are used. In FIG. 1, the retractor assembly 10 is shown in a first position. The retractor assembly 10 includes the first arm 14 and the second arm 18. The first arm 14 includes the first plate 22a and the second plate 26a. The first plate 22a is positioned in line with the second plate 26a, and the first and second plates 22a, 26a define some of the plurality of receiving wells 34. Similarly to the first arm 14, the second arm 18 includes the first plate 22b and the second plate 26b. The first plate 22b is positioned in line with the second plate 26b, and the first and second plates 22b, 26b define the remainder of the plurality of receiving wells 34.

Each of the receiving wells 30 may be coupled with retractor blades 48, as shown in FIG. 1. The blades 48 may be positioned so that one side of the blade 48 is slidable between the first plate 22a, 22b and the second plate 26a, 26b within the slot 30. In some examples, the retractor blades 48 may be bolted to one of the first arm 14 and the second arm 18. In other examples, the retractor blades 48 may be configured to couple to the retractor assembly 10 using a press fastener. When the retractor assembly 10 is in the first position, the retractor blades 48 may be positioned to overlap.

Retractor blades 48 may additionally or alternatively be coupled with a receiving slot 38 positioned on a midsection 84 of each of the first arm 14 and the second arm 18. It is contemplated that the receiving slot 38 may be replaced by receiving wells 34 or disposed at different locations (e.g., different from the midsection 84) along the length of the first arm 14 and/or second arm 18 without departing from the scope of the present disclosure. The receiving slot 38 may be configured to allow a retractor blade 48 to move laterally along one of the first arm 14 and the second arm 18 without detaching the retractor blade 48 from the retractor arm 14, 18, or to be refastened, changing the angle of the handle 102 of the retractor blade with respect to the retractor arm 14, 18. It is also contemplated that a receiving slot 38 may be used in place of any of the plurality of receiving wells 34 without departing from the scope of the present disclosure, allowing multiple receiving slots 38 to be used on the retractor assembly 10.

Referring now to FIG. 2, the retractor assembly 10 is shown in a second position. The second position, as shown in FIG. 2, may be an expanded position, where, in use, the retractor blades 48 are configured to retain a surgical incision open, permitting access to the underlying tissues and organs. The eccentric quick-lock cam lever 42 is configured to secure the retractor assembly 10 in the first position (FIG. 1) and the second position (FIG. 2). The cam lever 42 can also secure the retractor assembly 10 in any position between the first position and the second position. This provides a wide range of movement that allows the retractor assembly 10 to be used in various applications. The cam lever 42 operates about a pivot 90 where the first portion 22b of the second arm 18 is stacked over the first portion 22a of the first arm 14. This positions the second portion 26b of the second arm 18 under the first portion 22a of the first arm 14 and the second portion 26a of the first arm 14 on the furthest away from the cam lever 42. It is contemplated that the stacking of the first and second portions 22a, 22b, 26a, 26b is exemplary only and may be adjusted or alternated without departing from the scope of the present disclosure.

To unlock the retractor assembly 10 for movement, the cam lever 42 may be raised and rotated in a first direction to loosen a pivot 90. The first arm 14 and the second arm 18 are then rotatable about the pivot 90. When the desired position is reached, the cam lever 42 is rotated in a second direction, where the second direction is opposite the first direction. When the cam lever 42 is tightened, the cam lever 42 is then lowered to sit flush with one of the first arm 14 and the second arm 18. As shown in FIG. 2, the retractor assembly may be able to create an opening up to about 21 inches wide, with a vertical dimension of about 6 inches, when the cam lever 42 has been locked in a fully opened (e.g., 180 degrees) position. As the angle of the first arm 14 and the second arm 18 decreases from 180 degrees, a larger vertical dimension to the retracted region may be obtained, which decreasing the width of the surgical opening proportionately.

Referring now to FIGS. 3-6, in some other embodiments of a retractor assembly 10, the first arm 14 may define an arched guide 94 configured to guide the movement of the second arm 18. The guide 94 may be configured to receive a pin 98 operably coupled to the second arm 18 and may limit the movement of the first and second arms 14, 18 about the pivot 90 when adjusting the cam lever 42. When the pin 98 is flush with one end of the guide 94, the retractor assembly 10 is in the first position. When the pin 98 is flush with the other end of the guide 94, the retractor assembly 10 is in the second position. The length of the guide 94 may be determined by the desired amount of movement of the first arm 14 and the second arm 18.

Figure 3:
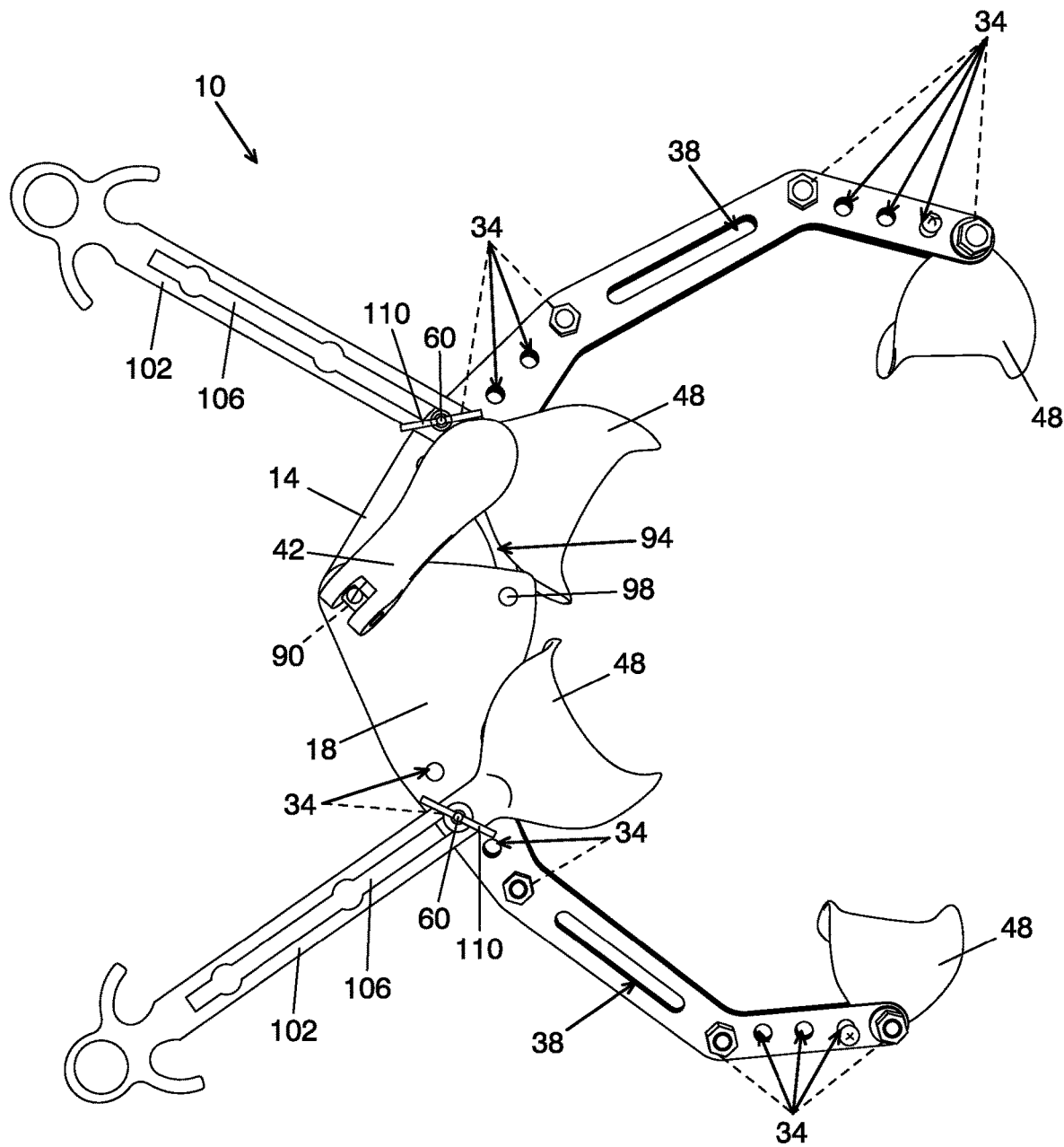
FIG. 3 is a photographic representation of a top view of a self-retaining retractor having multiple retractor blades with handles in exemplary positions according to some embodiments of the disclosure.
Figure 4:
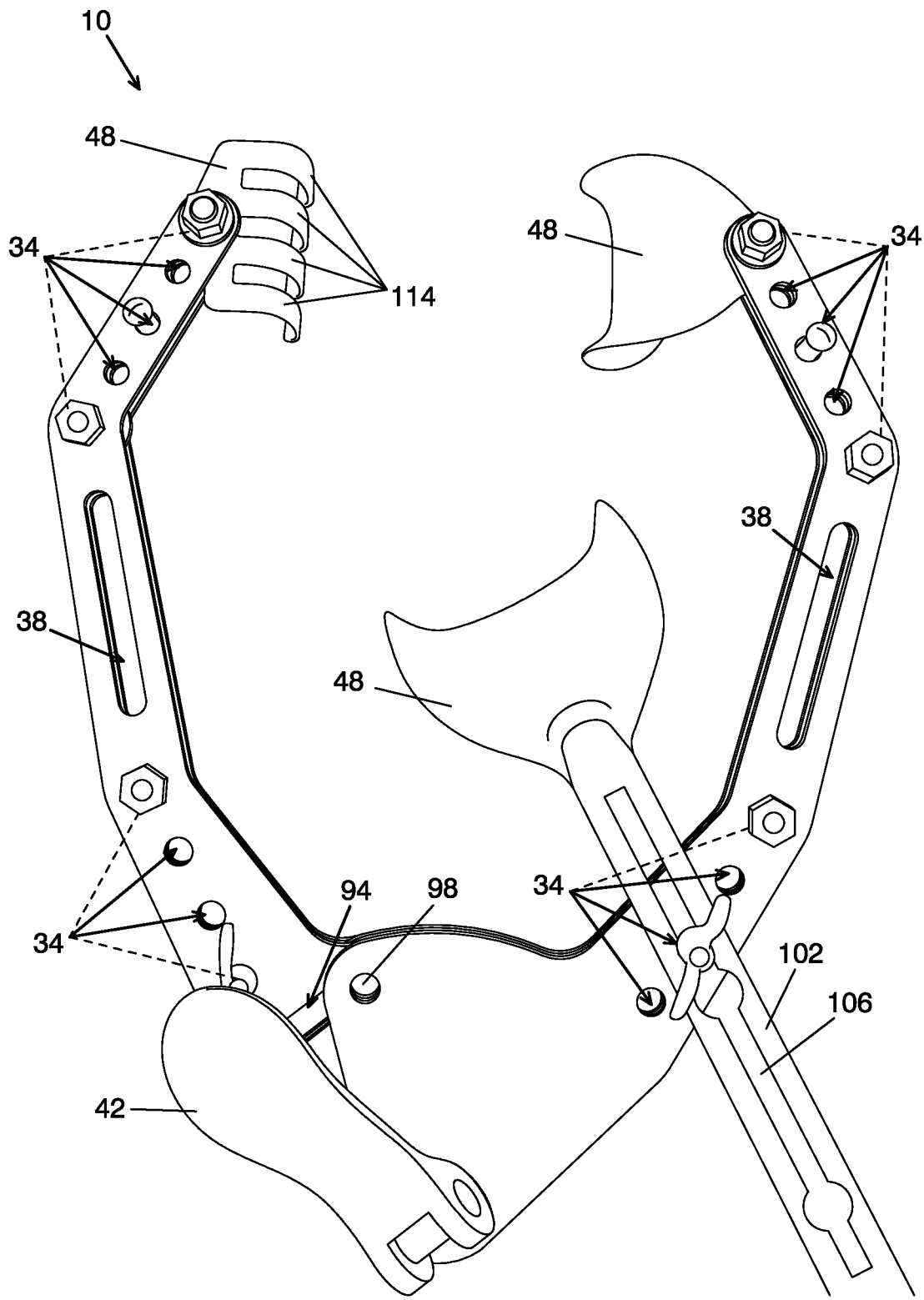
FIG. 4 is a photographic representation of a top perspective view of a self-retaining retractor having multiple retractor blades in exemplary positions according to some embodiments of the disclosure.
Figure 5:
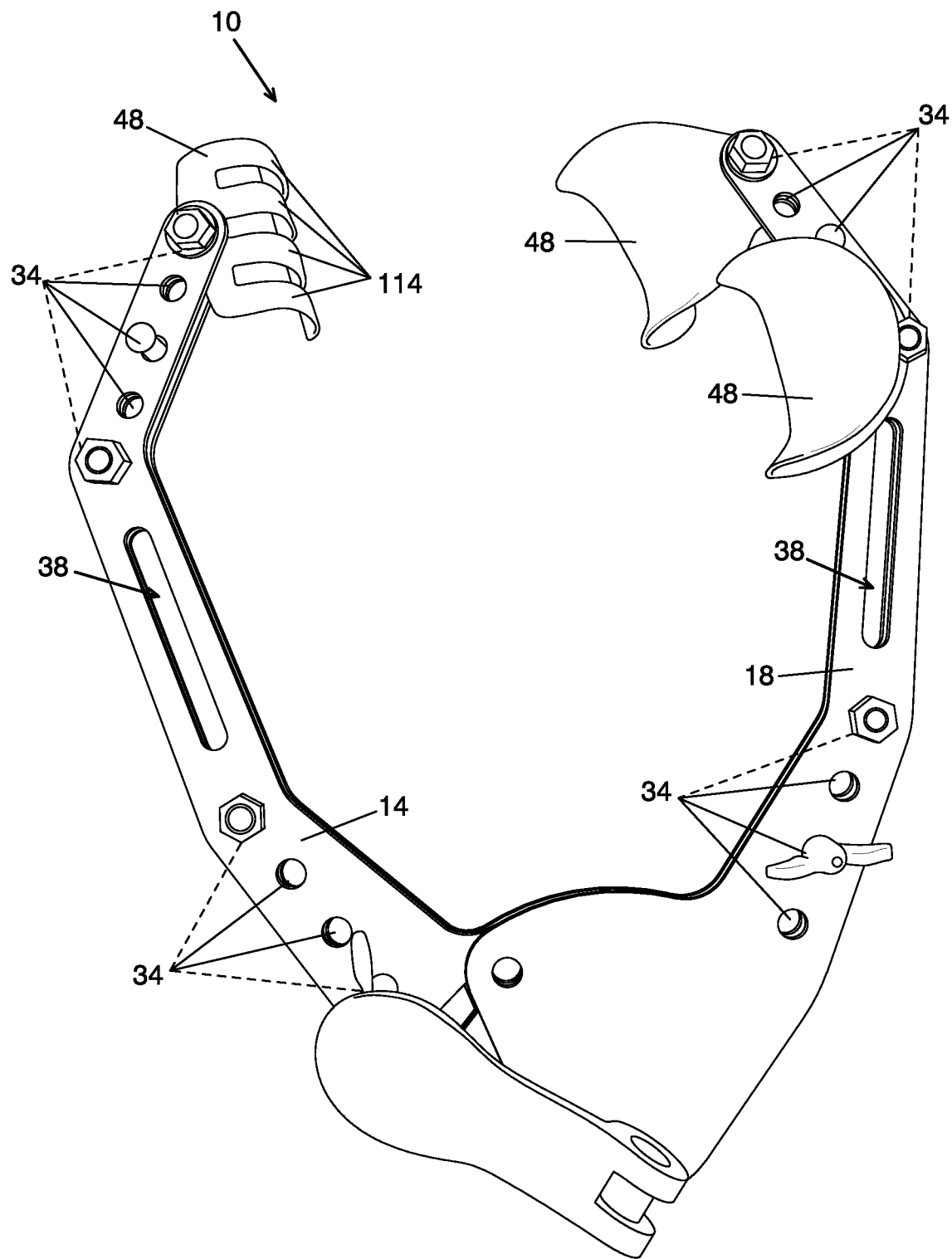
FIG. 5 is a photographic representation of a top perspective view of a self-retaining retractor having multiple retractor blades in exemplary positions according to some embodiments of the disclosure.
Figure 6:
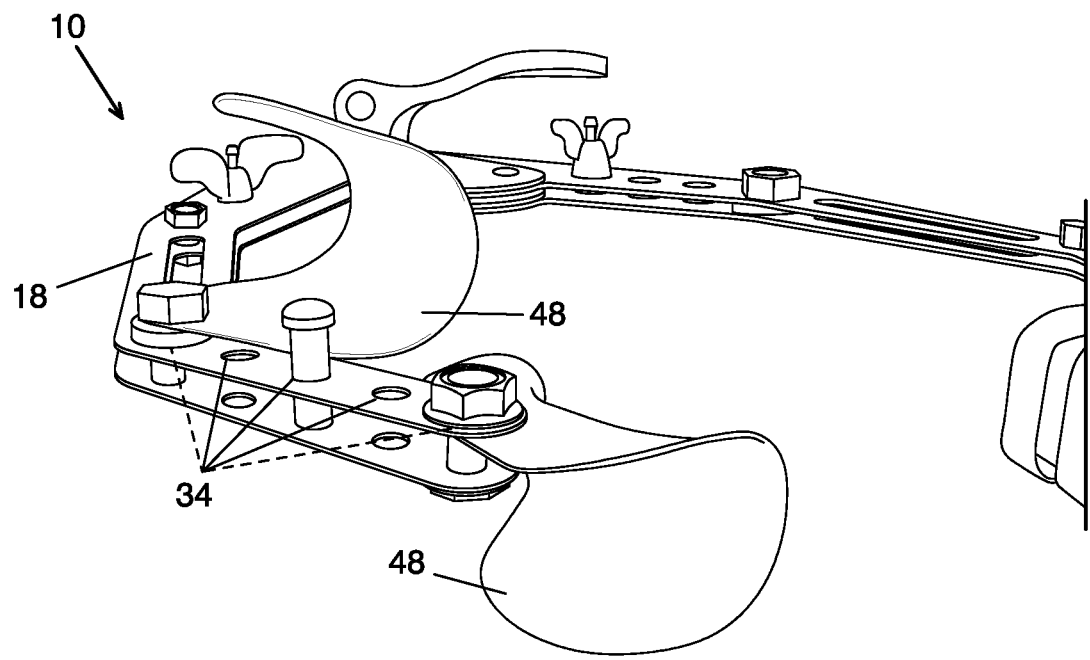
FIG. 6 is a photographic representation of a side perspective view of the self-retaining retractor of FIG. 5 according to some embodiments of the disclosure.

As shown in FIGS. 3 and 4, various forms of retractor blades 48 may be used. In some examples, the retractor blades 48 may include handles 102. When the handle 102 defines a channel 106, the channel may be operably coupled to one of the receiving wells 34 or receiving slots 38 by one of the fasteners 60. The fastener 60 may include a winged bolt 110 for easy and rapid adjustment of the retractor blade 48 along the length of the channel 106 of the handle 102. In other examples, the retractor blade 48 may include a plurality of extensions 114 rather than a single face. It will be understood that other variations of retractor blades 48 may be used with the retractor assembly 10 without departing from the scope of the present disclosure. Additionally, as shown in FIGS. 5 and 6, the retractor blades 48 may be operably coupled with any one of the receiving wells 34 or the receiving slot 38. The retractor blades may be operably coupled to one of the first portions 22a, 22b or one of the second portions 26a, 26b to provide connections for the retractor blades 48 that position them extending upward from the retractor assembly 10 or downward from the retractor assembly 10. Additionally, it will be understood that any number of retractor blades 48 may be used, based on the desired application of the retractor assembly 10, without departing from the scope of the present disclosure.

Figure 7:
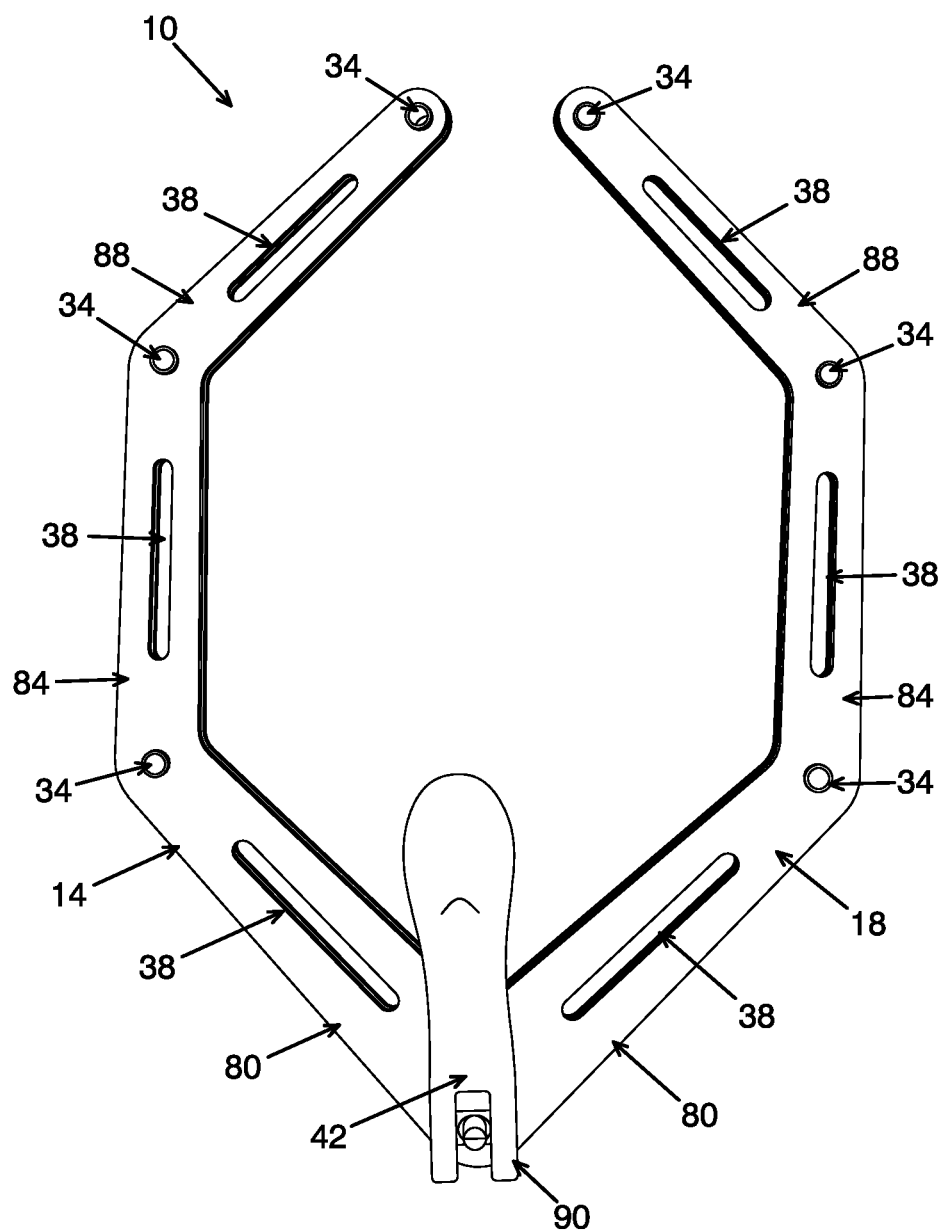
FIG. 7 is a photographic representation of a top perspective view of a self-retaining retractor according to some embodiments of the disclosure.
Figure 8:
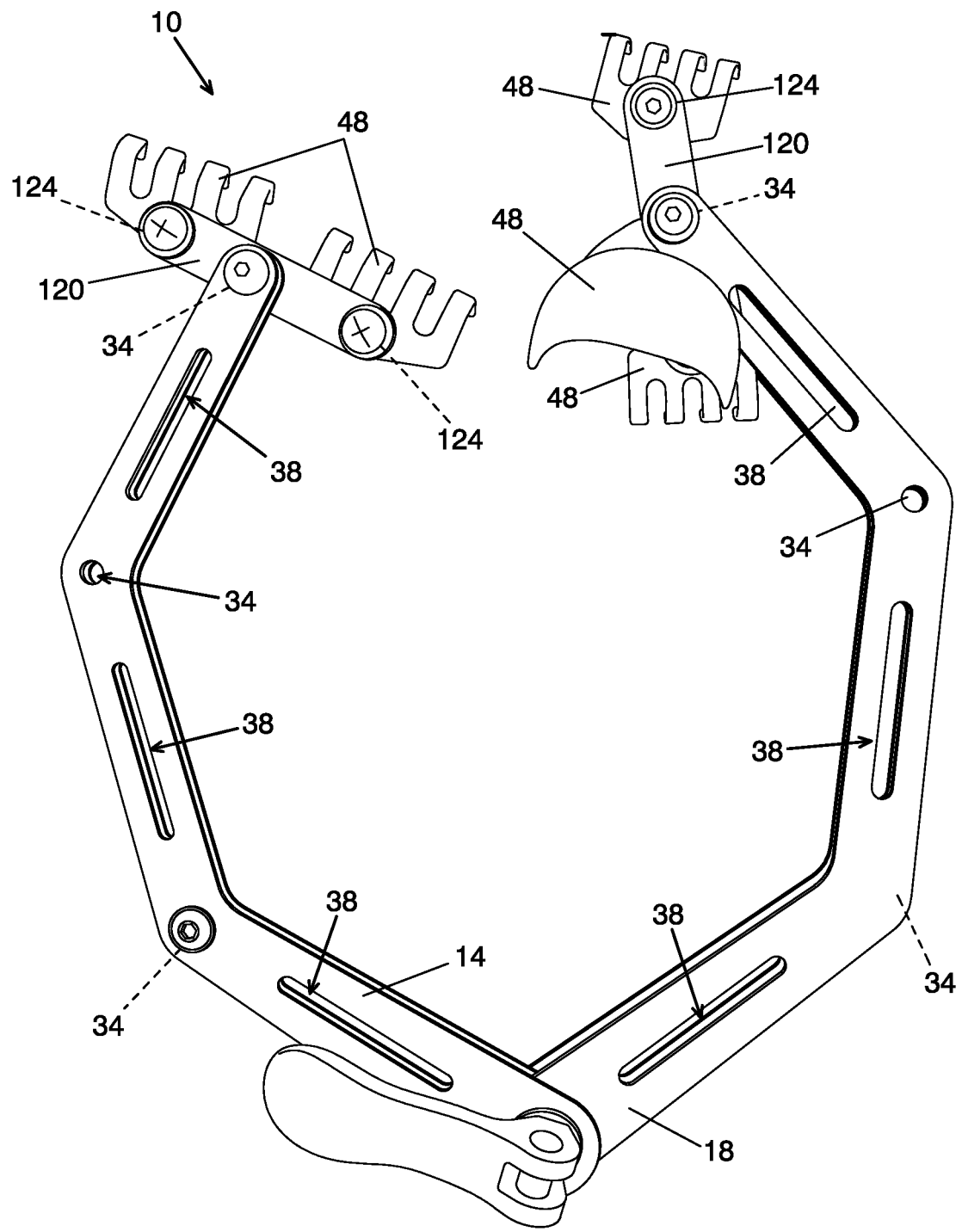
FIG. 8 is a photographic representation of a top perspective view of a self-retaining retractor having a self-positioning arm according to some embodiments of the disclosure.
Figure 9:
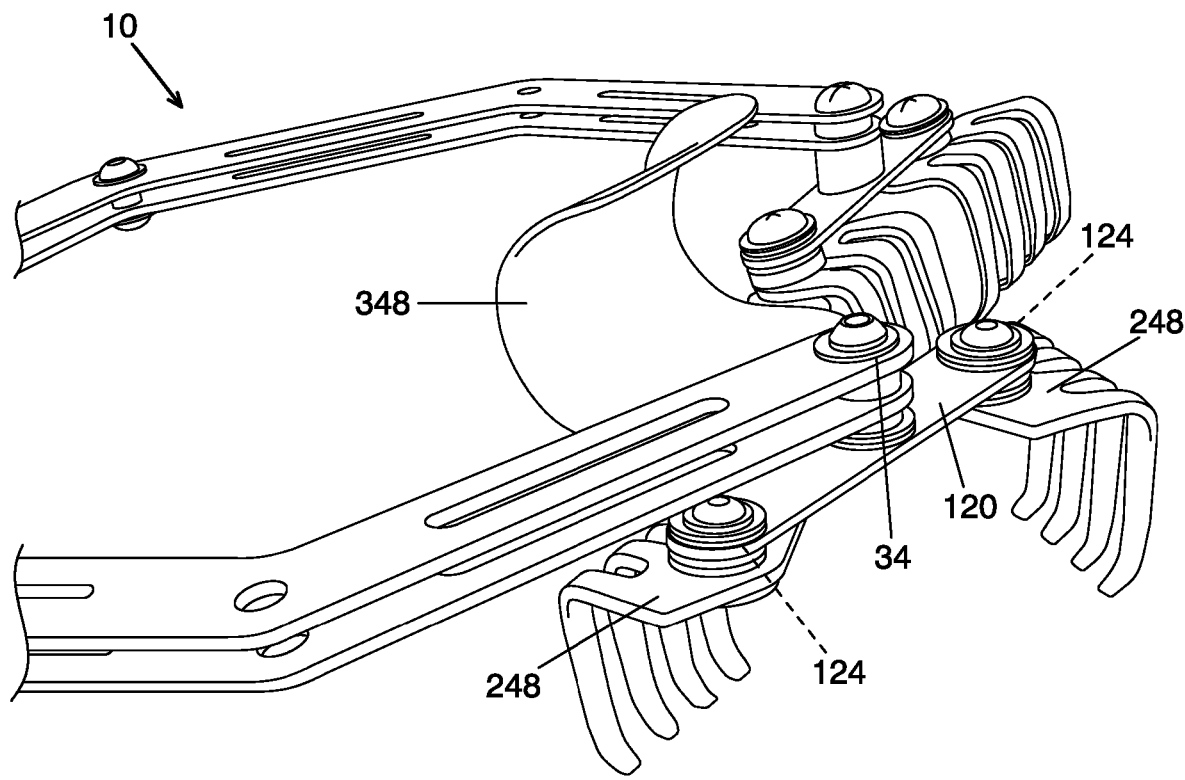
FIG. 9 is a side perspective view of a portion of the self-retaining retractor of FIG. 8.

Referring now to FIGS. 7-9, other embodiments of a retractor assembly incorporating an eccentric quick-lock cam lever 42 are shown. FIG. 7 shows a retractor assembly (with no retractor blades attached) that may be adjustably locked as described above for the similar retractor assembly of FIGS. 1-2. The retractor assembly 10 may have any of the features of a retractor assembly as described above, and further includes a first arm 14 having a first end 80, midsection 84, second end 88. Each of the first end 80, midsection 84, and second end 88 contains a receiving slot 38, and at the intersection of the first end 80 with the midsection 84 and the intersection of the second end 88 with the midsection 84, each arm 14, 18, includes a well 34. The eccentric quick-lock cam lever 42 is located at the pivot 90, and controls the extent of opening of the first arm 14 from the second arm 18. In this embodiment, there is no widened region around pivot 90 on first arm 14 and second arm 18. This configuration may provide more desirable visibility in some applications.

In FIG. 8, a retractor assembly 10 like that of retractor assembly 10 of FIG. 7 is shown which may include a self-positioning rotating arm 120 that may be rotatably coupled to one of the plurality of receiving wells 34 of the first arm 14. The self-positioning arm may include a plurality of receiving wells 124 configured to operably couple retractor blades 48 to the self-positioning arm 120. In some other examples, the self-positioning arm 120 may be fixed to prevent rotation about the receiving well 34. The retractor blades 48 may further be rotatable about the receiving wells 124 of the self-positioning arm 120 to allow a wide range of movement and visual options. In FIG. 8, the first arm 14 includes a self-positioning arm 120 including two sets of retractor blades 48, and the second arm 18 includes a self-positioning arm 120 attached via well 34 of the second end of arm 18, where the self-positioning arm includes two sets of retractor blades. A third retractor blade 48 is also attached via well 34 of the second end of arm 18.

In FIG. 9, a portion of the retractor 10 of FIG. 8 shows the variety of retractor blades mentioned above. The rotatable coupling of the self-positioning arm 120 through receiving well 34 is shown, as well as the two sets of rotatable retractor blades 48, each rotatably coupled through receiving wells 124 of self-positioning arm 120, extending downward in this view. The two sets of retractor blades 48, may each be a retractor blade 248, having individual finger extensions for holding back incised tissues. There may be 2, 3, 4, or more finger extensions, and the length of the finger extensions may vary. In some embodiments, each of the finger extensions of a retractor blade 248 may be selected to have a length suitable for the depth of the desired surgical incision and may be from about 0.1 inch to about 5 inches, or any length therebetween. In some other embodiments, the length of the finger extension may be longer than 5 inches. Extending above the arm 14 is the third retractor blade 48. As seen here, the third retractor blade 48 may be a cupped single blade 348. The cupped portion of the retractor blade 348 may be useful to hold back intestines or other organs when retrieving organs for transplantation, and may have no sharp edges at all. The cupped retractor blade 348 and the retractor blade 248, having finger extensions may be used in tandem, for example, where the retractor blade 248 holds the surgical incision open and the cupped retractor blade 348 holds portions of the intestines aside during organ retrieval surgical procedures. The cupped retractor blade 348 may be particularly useful in organ retrieval.

Figure 10A:
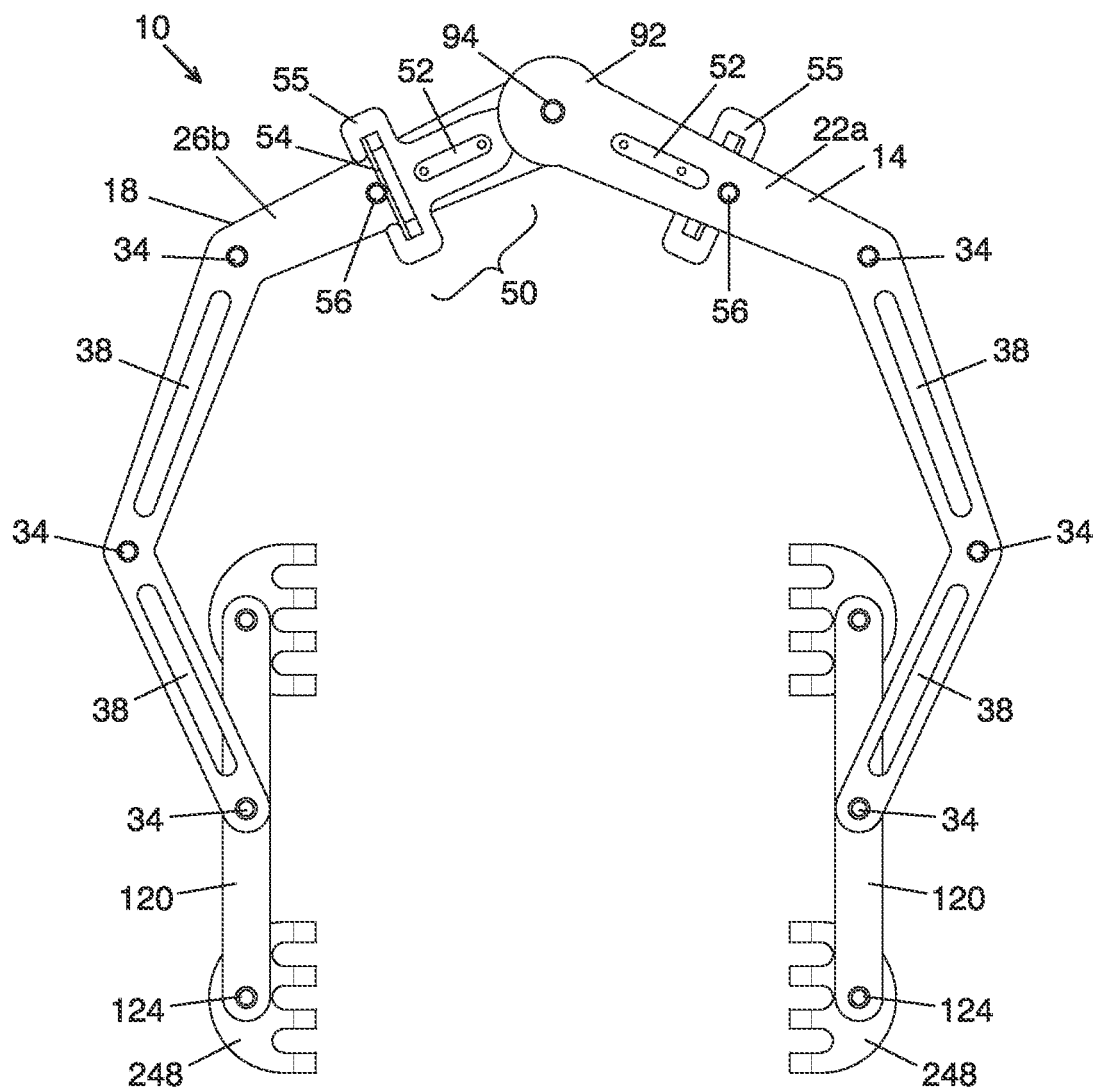
FIG. 10A is a graphical representation of a top perspective view of a self-retaining retractor having a quick release plate according to some embodiments of the disclosure.

FIGS. 10A-B to 16 and 19-22 show yet another embodiment of a retractor assembly 10, which includes a quick release ratcheting mechanism 50 as the locking mechanism. FIG. 10A shows a retractor assembly, partially assembled to show some of the details of the quick release mechanism (shown as a quick release plate) 50. As shown in FIG. 10A, plate 22a of arm 14 is shown, while only the lower plate 26b of arm 18 is shown, so that details of quick release plate 50 may be seen. Quick release plate 50 includes a guide bar 52, which fits into a slot (not shown) of plate 26b of arm 18. The guide bar 52 assists in aligning the quick release plate 50 along the arm 18 as it is engaged or repositioned. Biasing element 54, which may be a nitinol wire, a spring, an elastic member, or the like, is biased against restraining pin 56 to hold the quick release plate against the pivot 90 (not shown here). Tabs 55 are configured to be grasped while readjusting the angle of the arms 14, 18 to each other. The locking mechanism including the quick release plate may be a self-locking mechanism. The locking and adjustment mechanism is as described in greater detail below in FIG. 16. Generally, the quick release plates 50, present on each of arm 14 and 18, may be engaged against a portion of the opposing arm (not shown in FIG. 10A) to select and lock a selected position of the arms 14, 18 with respect to each other. Advantages of the quick release plates 50 include the ability to pull the retractor arms open without any requirement to make a separate locking gesture; the retractor assembly stays open, e.g., the locking mechanism is self-locking. The quick release plate of FIGS. 10A-B to 16 and 19-22 aid in the speed of use and general facility in operation. The two arms are held adjustably together at pivot region 92, using a fastener 94 at the pivot. The fastener may be any kind of fastener permitting rotatable motion of arm 14 relative to arm 18, and may be a bolt, a pin, a press fitting, a quick connect fitting, a telescoping barrel fitting, or any suitable fastener permitting rotation as is known in the art. The retractor assembly 10 of FIG. 10A may have any of the other features of a retractor assembly of FIGS. 1-9 and 11-25, and similar features have similar reference numbers.

Figure 10B:
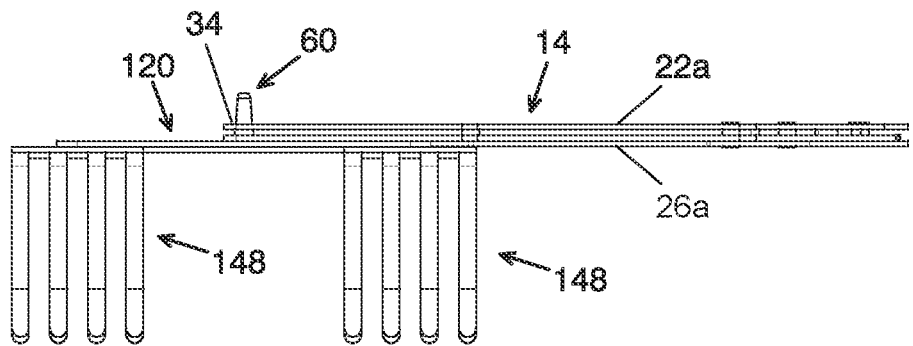
FIG. 10B is a graphical representation of a side perspective view of a retractor blade attached to an arm of a self-retaining retractor according to some embodiments of the disclosure.

FIG. 10B shows a side perspective view of the retractor blades 248 attached to self-positioning rotating arm 120, and connected via the arm 120 to arm 14 via a fastener 60 inserted into well 34 of arm 14. FIG. 10B shows the two plates 22a and 26a of arm 14. The finger extensions 148 of the retractor blade 248 have a length selected to be optimized for the surgical use intended, as described.

Figure 11:
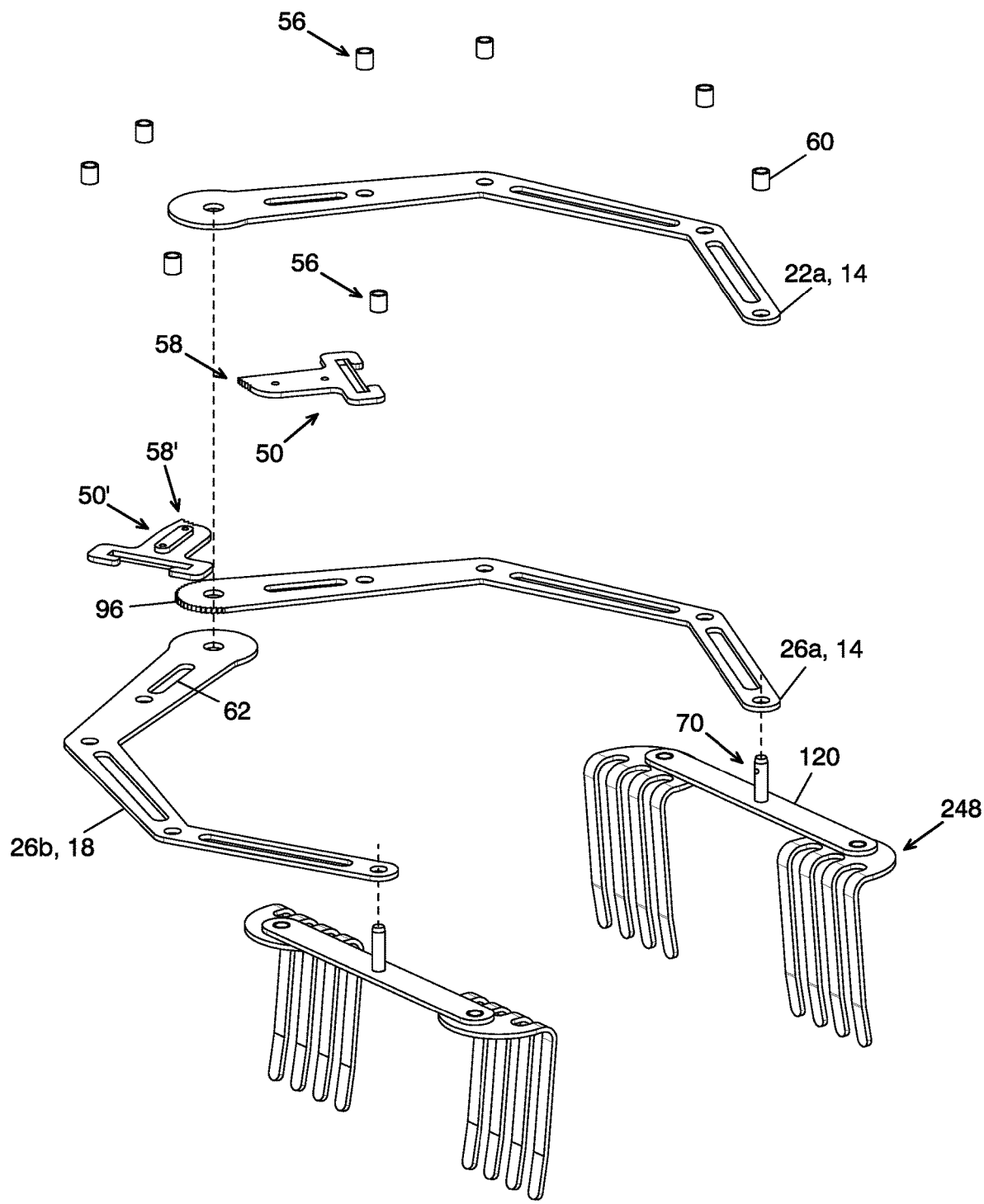
FIG. 11 is a graphical representation of an exploded view of a self-retaining retractor according to some embodiments of the disclosure.

FIG. 11 is an exploded view of the partially assembled retractor assembly 10 of FIGS. 10A and 10B. Plates 22a and 26a of arm 14 may be aligned and fastened at pivot 90 (fastener not shown), with a first quick release plate 50 interspersed. Pins 56 may pass through plates 22a and 26a to place quick release plate 50 in tension, by biasing strip 54. The pawl 58 is the portion of quick release plate 50 that engages with a set of ratchet teeth of the opposite arm 18 (not shown). The second quick release plate 50' is disposed on plate 26b of arm 18, and the guide bar 52 fits through guide slot. Pawl 58 engages the set of ratchet teeth 96 of plate 26a of arm 14, and the quick release plate 50 is held in tension against the set of ratchet teeth 96 by biasing strip 54 and pins like pins 56 (not shown here). Also shown is the attachment of self-positioning rotating arm 120 via a rotatable coupling pin 72, and retractor blades 248 attached to the self-positioning arm 120.

FIG. 12A is a top perspective view of dimensions and features of an exemplary plate 22C of an arm 14 or 18. At least one of the two, three, or more plates aligned to form an arm 14 and/or arm 18 may be like the plate of FIG. 12A. Plate 22C is like plate 26a of FIG. 11 and FIG. 10A. The dimensions shown in FIG. 12A are in inches. For example, the first end 80 may have a length, excluding the set of ratchet teeth 96, of about 5.50 inches; the midsection 84 may have a length of about 5.0 inches, and the second end 88 may have a length of about 4.5 inches, exclusive of the rounded end of the plate. However, the dimensions shown are but one example, and many variations may be suitably chosen. The angle between the first end 80 and midsection 84 may be selected to be about 135 degrees, and the angle between the midsection 84 and the second end may be about 135 degrees, and form a C-shaped opening. FIG. 12B shows the side perspective view of the plate of FIG. 12A, and shows that it may have a thickness of about 0.105 inches.

Figures 13A, 13B:
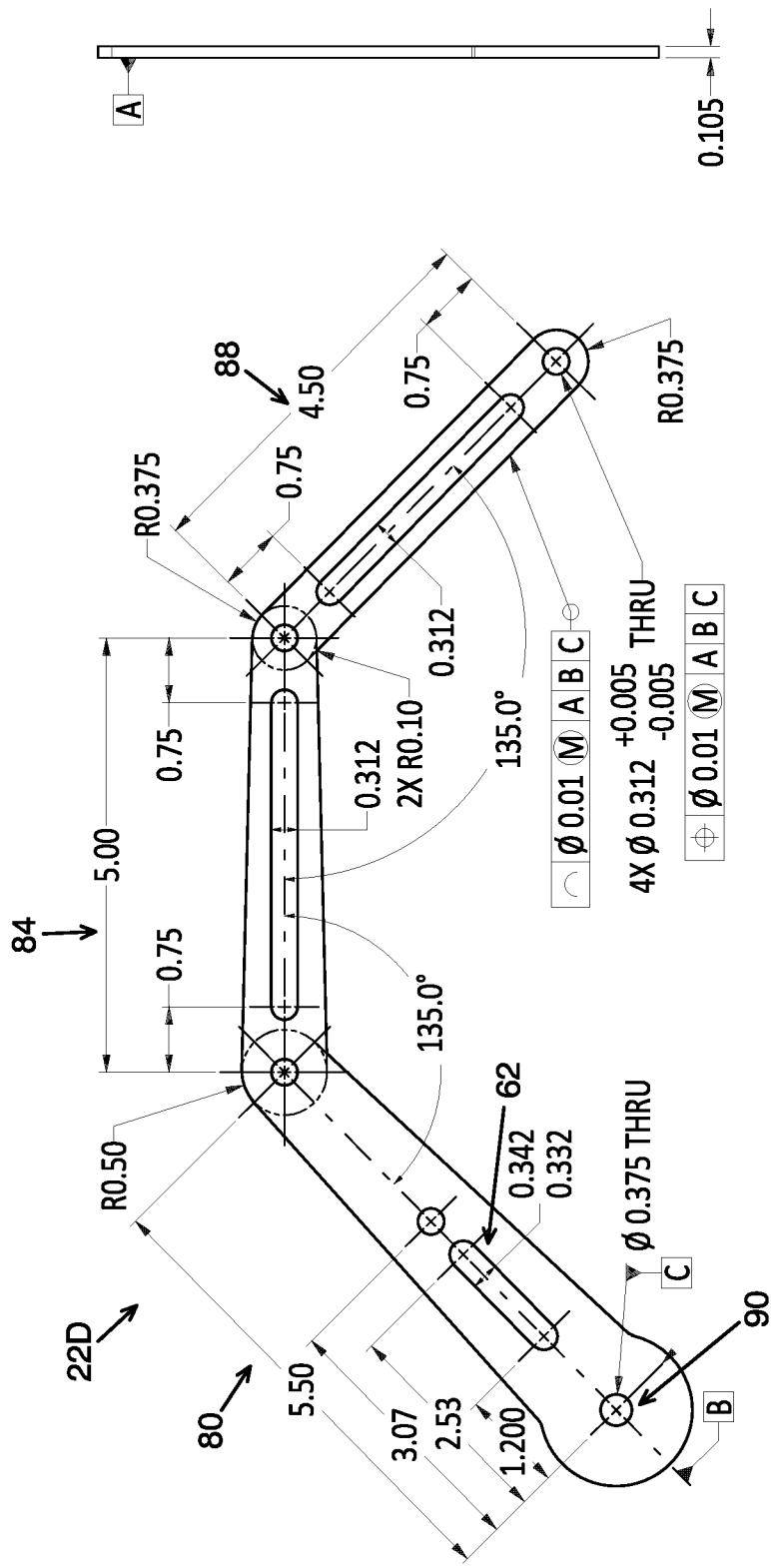
FIGS. 13A and 13B are graphical representations of a top perspective view and a side perspective view respectively of a plate of an arm of a self-retaining retractor according to some embodiments of the disclosure.

FIG. 13A is a top perspective view of dimensions and features of an exemplary plate 22D of an arm 14 or 18. At least one of the two, three, or more plates aligned to form an arm 14 and/or arm 18 may be like the plate of FIG. 13A. Plate 22C is like plate 22a or 26b of FIG. 11 and FIG. 10A. The dimensions shown in FIG. 13A are in inches. For example, the first end 80 may have a length, excluding the rounded region extending past pivot point 90, of about 5.50 inches; the midsection 84 may have a length of about 5.0 inches, and the second end 88 may have a length of about 4.5 inches, exclusive of the rounded end of the plate. However, the dimensions shown are but one example, and many variations may be suitably chosen. The angle between the first end 80 and midsection 84 may be selected to be about 135 degrees, and the angle between the midsection 84 and the second end may be about 135 degrees, and form a C-shaped opening. Plate 22D has a guide slot 62 into which the guide bar of a quick release plate 50 or 50' may be disposed, and the length of the guide slot, exclusive of rounded ends, may be about 1.3 inches. FIG. 13B shows the side perspective view of the plate of FIG. 13A, and shows that it may have a thickness of about 0.105 inches.

FIGS. 14A-C show perspective views of the first release mechanism 50. FIG. 14A shows a perspective view and FIG. 14C a top view, of the first quick release plate 50, including quick release tabs 55 (forming a release on each side of the arm) extending outward from both sides of mechanism 50, and a bias (e.g., biasing strip 53), which may be a nitinol wire, an elastic membrane, a spring or any other elastic member material. Guide bar 52 projects slightly upwardly on one side (and may extend on the opposite side as well, not shown) from the horizontal plane of the quick release plate 50, and is configured to fit into a guide slot 62 on the plates forming the arm 14 or 18. The guide bar may be integral to the quick release plate or attached, e.g., secured to the quick release plate 50 by one or more fasteners 53, which may be any suitable kind of fastener such as a screw, or other fastening device. The quick release plate may include a pawl 58, which is configured to mate with the set of ratchet teeth 96 of a plate of arm 14 and/or arm 18. When engaged with the set of ratchet teeth 96, pawl 58 prevents movement of arms 14 and 18 relative to each other in one direction (e.g., clockwise) while allowing relatively easy rotation in the opposite direction. When released by the quick release, the pawl may permit rotation by disengaging from the set of ratchet teeth 96 of the plate of arm 14, 18 to permit closing of the retractor assembly; the retractor may be opened by the application of fairly low force, allowing the pawl to ratchet over the set of ratcheting teeth. Contoured cutaway region 57 may be configured to prevent interference and to permit rotation when the quick release plate disengages pawl 58 from the set of ratchet teeth 96. Similarly, the set of ratcheting teeth may only extend partially around the circular end of the portion of the arm including the set of ratcheting teeth, allowing the device to freely move the arms at some angles.

FIG. 14C shows a side view of quick release plate 50, showing the guide bar 52, extending outward on both sides from the horizontal plane of the quick release plate 50. The quick release plate (including the guide bars) may be lubricated for easy movement within the arms or they may include a lubricious surface (e.g., coating, etc.).

Figure 15A:
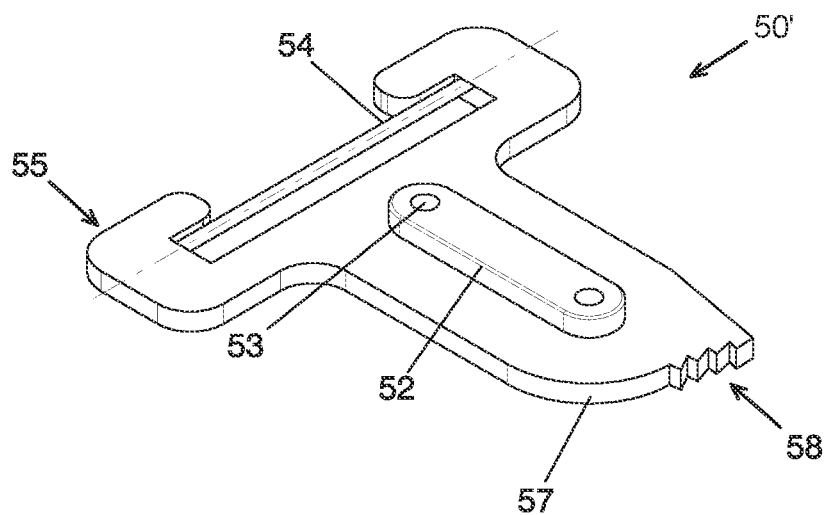
FIGS. 15A to 15C show examples of a perspective view, a top view and a side view of one variation of a first quick release mechanism (e.g., quick release plate) according to some embodiments of the disclosure.
Figure 15B:
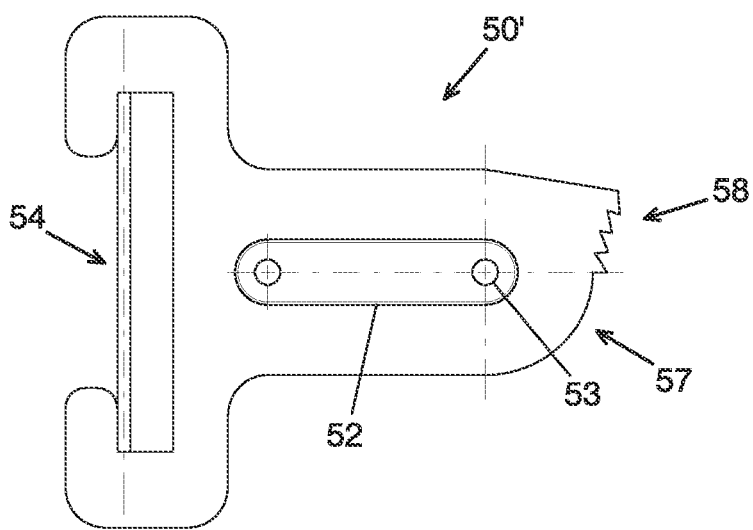
Figure 15C:
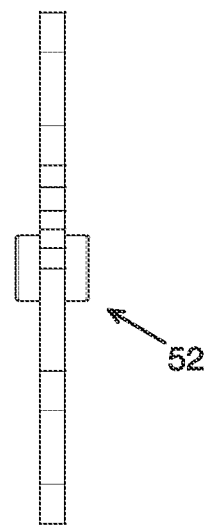

FIGS. 15A-C show perspective views of the second release mechanism 50'. FIG. 15A shows a perspective view and FIG. 15C a top view, of the second release mechanism 50' including quick release tabs 55 extending outward from both sides of mechanism 50', and a bias (e.g., biasing strip 53), which may be a nitinol wire, an elastic membrane, a spring or any other elastic member material. Guide bar 52 extends upwardly and below (not shown) from the horizontal plane of the second release mechanism 50', and is configured to fit into guide slots 62 of plates forming arm 14 or 18. The guide bar 52 is secured to the second release mechanism 50' by one or more fasteners 53, which may be any suitable kind of fastener such as a screw, or other fastening device. The second release mechanism 50' incudes pawl 58, which is configured to mate with the set of ratchet teeth 96 of a plate of arm 14 and/or arm 18. When engaged with the set of ratchet teeth 96, pawl 58 prevents movement of arms 14 and 18 relative to each other in one direction (e.g., "closing"), but permits relatively easy movement in the opposite (e.g., "opening") direction, as described above for FIGS. 14A-14C. When released by the second release mechanism 50' (release), e.g., by driving/sliding the quick release plate away from the pivot and compressing the bias, the pawl may disengage from the ratcheting teeth 96 of the plate of arm 14, 18 to permit closing of the retractor assembly. Contoured cutaway region 57 is configured to prevent interference and to permit rotation when the quick release plate disengages pawl 58 from the set of ratchet teeth 96. FIG. 15C shows a side view of quick release plate 50', showing the guide bar 52, extending outward on both sides from the horizontal plane of the q second release mechanism 50'.

FIG. 16 shows a portion of the quick release plate 50 or 50', engaged with the set of ratchet teeth 96 portion of a plate of arm 14 or arm 18 (only the ratchet teeth of the arm are illustrated; see FIG. 12 for an illustration of the entire arm). The pawl 58 of mechanism 50, 50' mates with the individual teeth 98 of the set of ratchet teeth 96, which are angular teeth having a more nearly vertical face on the clockwise facing facet of each tooth, and a less vertical face on the counterclockwise-facing facet of each tooth. The pawl 58 is held in tension by a bias (e.g., biasing strip 53) that pushes against the restraining pin 56 when at rest. The angles of the pawl 58 are complementary to the angles of the teeth 98 of the set of ratchet teeth 96 and when released from biasing (e.g., tension) against the set of ratchet teeth 96, permit counterclockwise movement of the set of ratchet teeth 96, controllably to a single tooth advance at a time, depending on the extent of relief of tension of the pawl 58. The relief from biasing force may be provided by pulling on tabs 55 to deflect biasing strip 54 to a second more deflected position against restraining pin 56, and moving the pawl out of engagement with the set of ratchet teeth 96. Thus, quick and controllable adjustment of the extent of pivoting about pivot 90 may be provided. In some variations, the biasing strip may extend further than shown in FIG. 16; for example the biasing strip 55 may extend the full length (shown in FIG. 16 as 2.5 mm) of the quick release plate. As mentioned, the dimensions shown are for illustration only; other dimensions may be used.

In normal operation, the ratcheting mechanism of the quick release plate and the opposite arm (e.g., the set of ratcheting teeth) may allow the arms to be opened with the application of very little force, but result in locking of the arms to prevent "closing" of the jaws formed by the arms. The extent of movement about pivot 90 may be controlled by the pitch of the toothed advance. For this example, the advance may be defined as a 5-degree pitch to the clockwise facing facet and an eight-degree pitch to the counterclockwise facing facet of the teeth of the set of ratchet teeth 96. When the retractor 10 is no longer needed, the biasing strip 54 may be deflected further to a third final deflected position against restraining pin 56 such that pawl 58 no longer engages the set of ratchet teeth 96 at all, and the arms 14 and 18 may be brought back to a closed position.

FIGS. 17A and B show the top and side views of guide bar 52, which fits into guide slot 62 of the plates of arms 14, 18 (not shown). The guide bar 52 is configured to move along the guide slot 62 as the quick release plate is deployed, keeping the quick release plate aligned with the arms 14, 18 and the set of ratchet teeth 96.

FIG. 18A is a top view of a retractor blade assembly configured as a hand or set of fingers, including an attachment bar 118, which in some embodiments may be a self-positioning rotating arm 120, having a receiving well 124 for coupling via a fastener to an arm 14, 18 of the retractor assembly 10. Another receiving well 124' shows a fastener attaching the retractor blade 248, having fingered extensions. FIG. 18B is a side view of the retractor blade 248. FIG. 18C is a side view of the finger extensions 148 of the retractor blade 248 of FIG. 18A, where the length of the finger extensions may be any suitable length as described herein.

FIGS. 19A-19D show a perspective view, a back view, and a top view of a retractor blade 348. FIG. 19D is a section view through line A-A of FIG. 19C. This variation of a retractor blade is shown as saddle-shaped and may be used to hold back and/or tissue against the relatively smooth surface.

Figure 20:
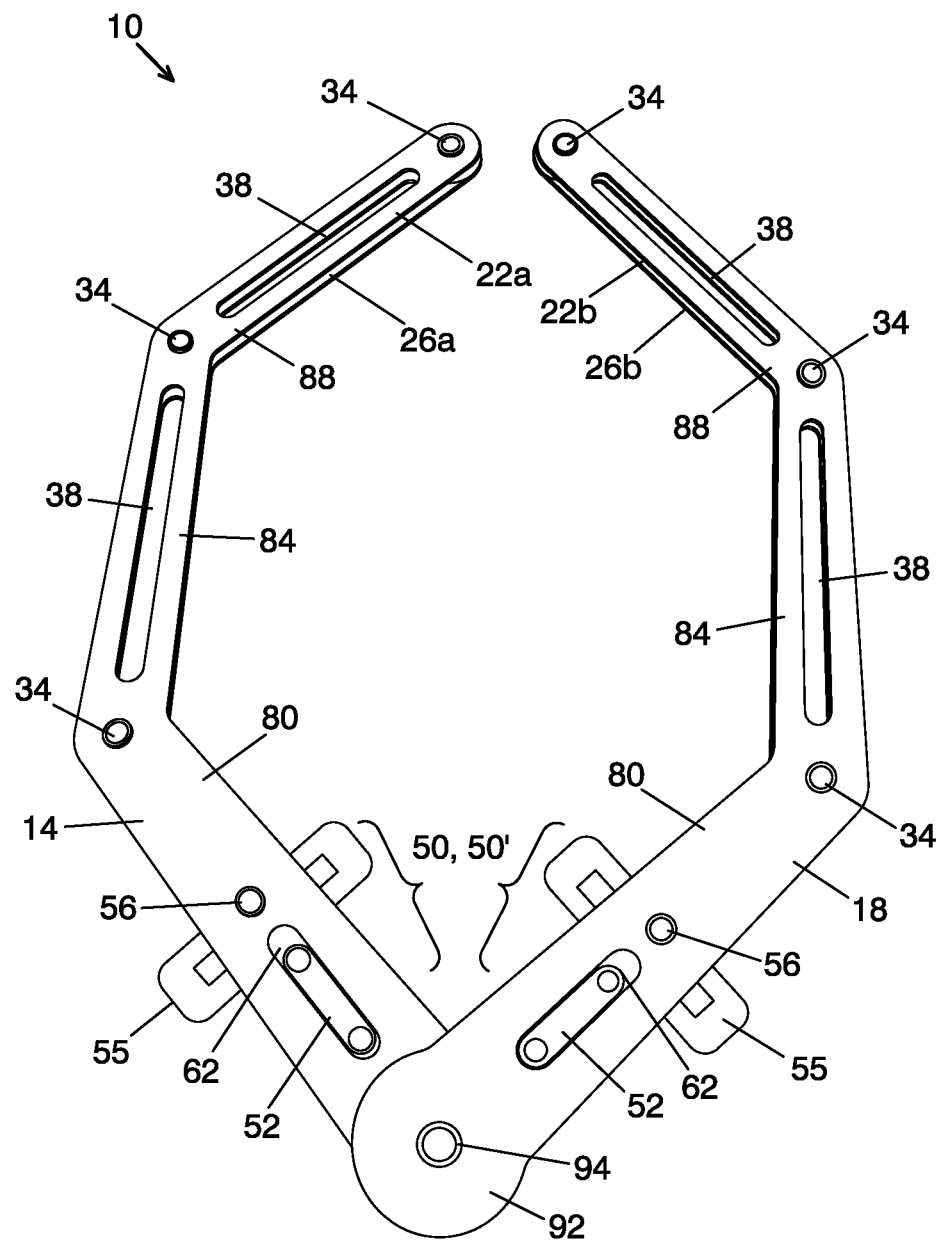
FIG. 20 and FIG. 21 are opposite faces of a retractor assembly having a quick release ratcheting mechanism according to some embodiments of the disclosure.
Figure 21:
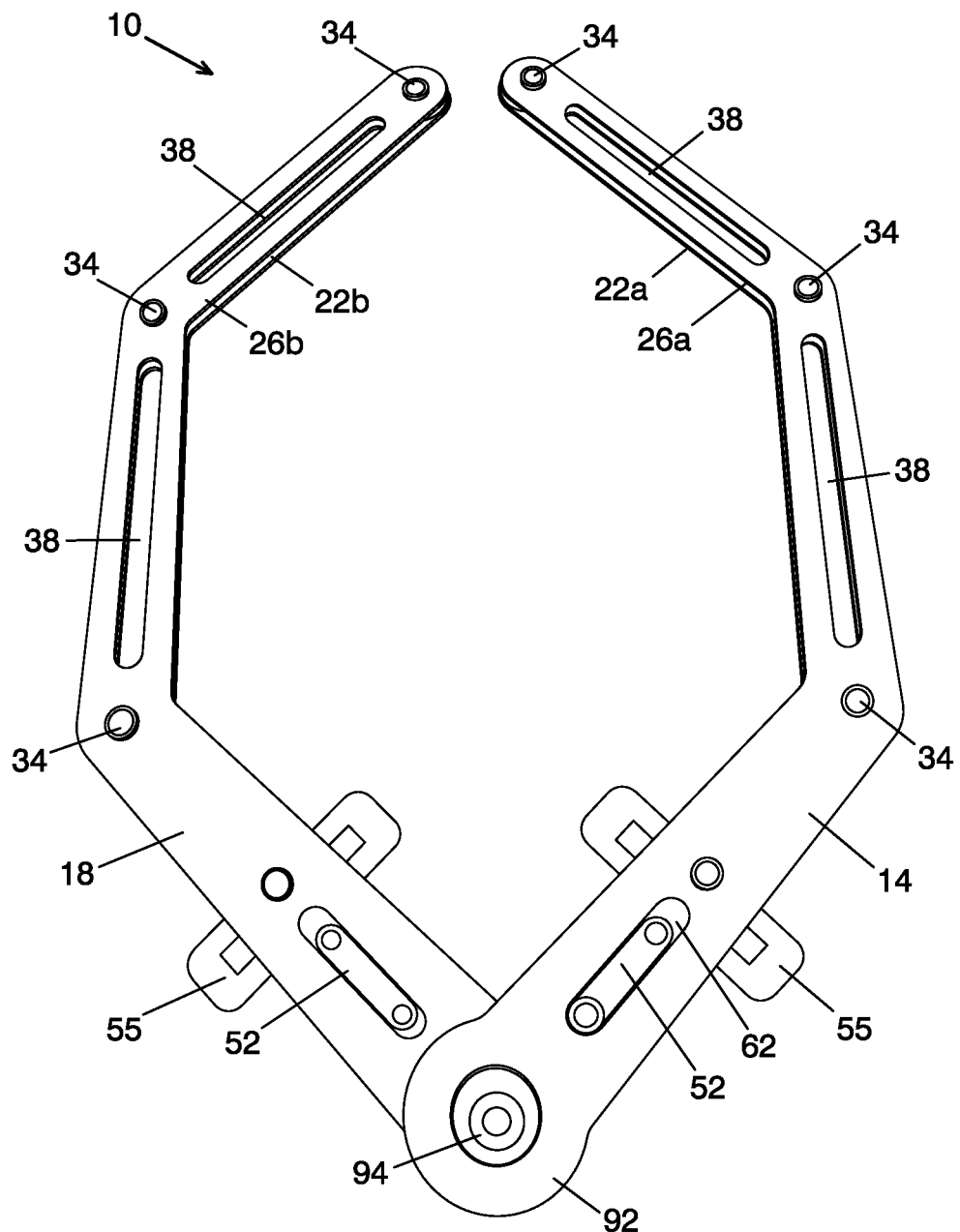

FIG. 20 shows a first side of another retractor assembly 10 having arm 14 and arm 18. The arms 14, 18 each include two plates. Arm 14 has an upper plate 22a and a lower plate 26a, separated by slot 30 (not shown). Arm 18 has an upper plate 22b and a lower plate 26b separated by slot 30 (not shown). In some other embodiments of the retractor assembly 10 of FIG. 20, there may be more than two plates, e.g., three plates, four plates or more, each separated from each other by a slot 30. Arms 14, 18 each have a first end 80, a midsection 84 and a second end 88, which may have any dimensions as described herein. There may be additional sections as well, as described herein. Additionally, while arms 14, 18 are shown having discrete changes of angles between each section, the arms may instead have a continuous curve or multiple curves. Arms 14, 18 form a C-shaped region. Arms 14, 18 have receiving wells 34 and receiving slots 38 configured to permit attachment of retractor blades or other components such as but not limited to a camera. The pivot region of retractor 10 of FIG. 20 has a bolt 94 as a pivot fastener permitting rotation of the two arms 14, 18, permitting adjustable opening and closing. The position of arms 14, 18 relative to each other is adjustable using quick release plates 50, 50', each of which is stacked within the plates of the respective arm and configured to engage a corresponding the set of ratchet teeth 96 of the other arm, as described above for FIG. 16. The quick release plates 50, 50' may be like any quick release plates 50, 50' described herein. The quick release tabs 55 of the quick release plates 50, 50' are visible, extending from the region of the slot 30, and the guide bar 52 is visible within the guide slot 62 of each upper plate visible here. FIG. 21 shows the opposite face of the retractor assembly 10 of FIG. 20, and therefore has all of the same features. Notable in this view is the washer portion of the pivot fastener 94

Figure 22:
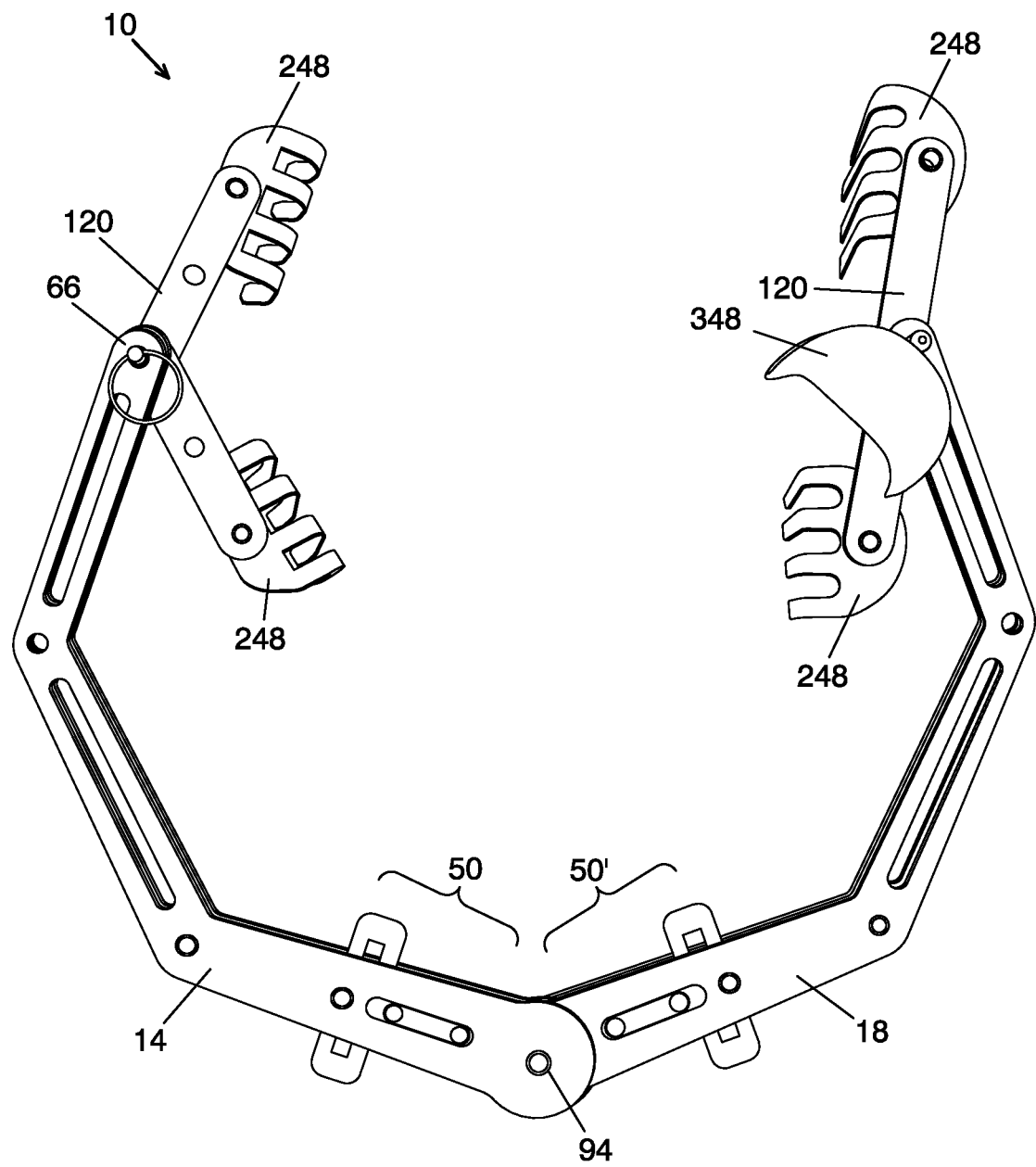
FIG. 22 is a photographic representation of a retractor assembly having a quick release ratcheting mechanism according to some embodiments of the disclosure, which is shown in a first opened position.
Figure 23:
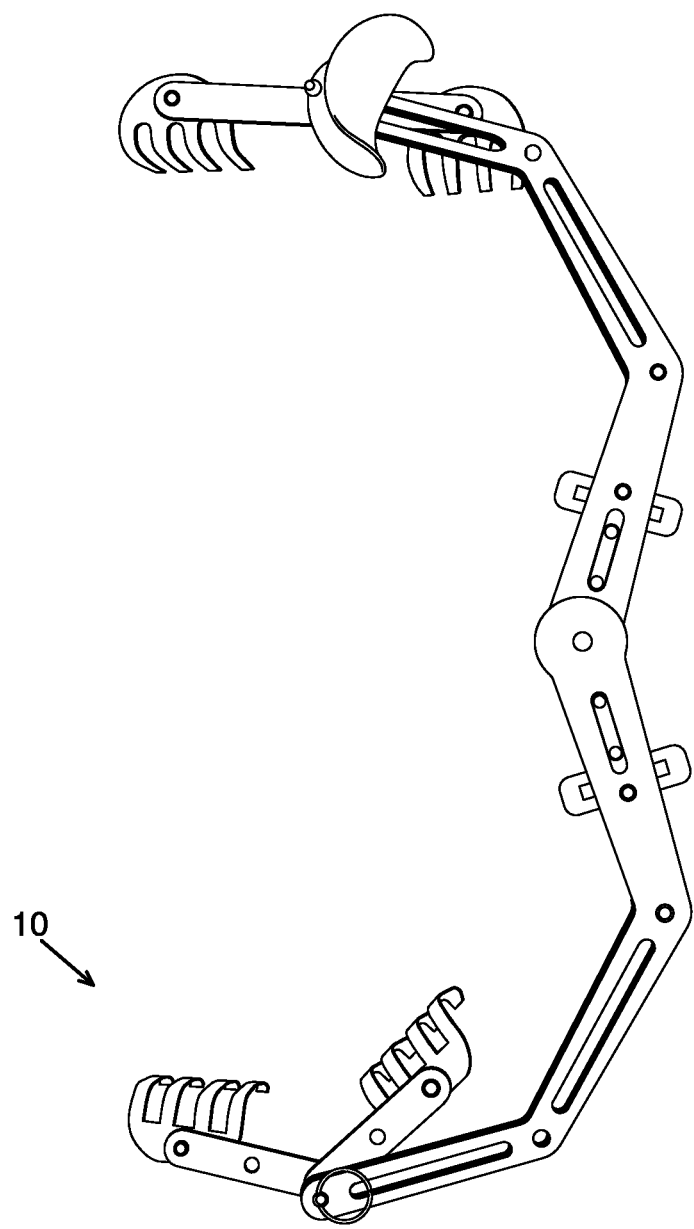
FIG. 23 is a photographic representation of the retractor assembly of FIG. 22, having a quick release ratcheting mechanism shown in a second opened position.

FIG. 22 shows yet another embodiment of a retractor assembly 10 including quick release plates 50, 50'. While not labeled, the retractor assembly 10 of FIG. 22 may have any of the features as described for FIGS. 20 and 21. However, the retractor assembly of FIG. 22 has a different pivot fastener 94 from that of FIGS. 20 and 21, having a press fastener instead of a bolt and washer fastener. In FIG. 22, the retractor assembly 10 is shown having a self-positioning rotatable arm 120 with two sets of retractor blades 248, attached to arm 14. The self-positioning rotatable arm 120 is releasably attached to arm 14 via quick connect 66 fastener, which is inserted into a receiving well 34, not visible here. Retractor assembly 10 of FIG. 22 has both a self-positioning rotatable arm 120 with two sets of retractor blades 248 and a retractor blade 348 attached to arm 18. As can be seen in FIG. 22, the retractor blade 348 and self-positioning arm(s) 120 may be positioned as needed, and the retractor blades 248 may also be rotatably attached to self-positioning arm 120. The retractor assembly 10 of FIG. 22 may have additional or different retractor blades attached at different location upon the retractor assembly as described herein; the specific implements shown in FIG. 22 are not intended to be limiting the retractor assembly in any way. In FIG. 22, the retractor assembly 10 is shown in a first partially open configuration. The retractor assembly 10 of FIG. 22 may be opened further or less as described in FIG. 16. FIG. 23 shows the retractor assembly of FIG. 22 in a second fully opened configuration, showing the extent of surgical working area possible with the retractor assembly 10.

Figure 24A:
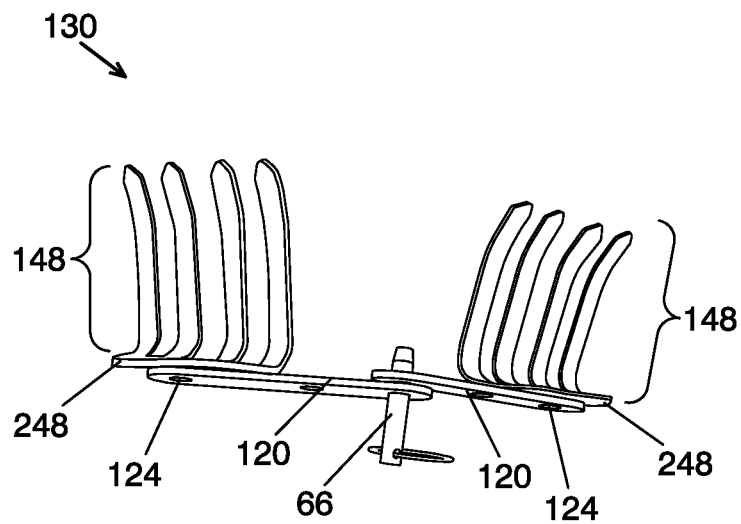
FIGS. 24A-24C are photographic representations of subassemblies for retractor blades according to some embodiments of the disclosure.
Figure 24B:
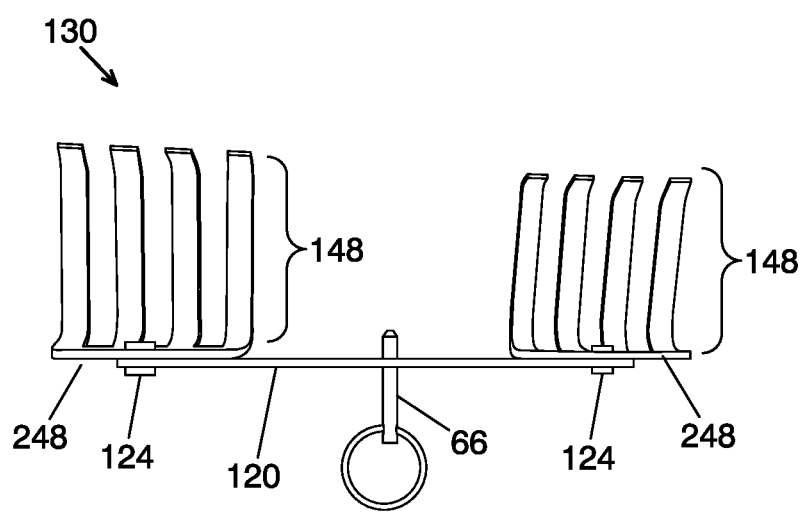
Figure 24C:
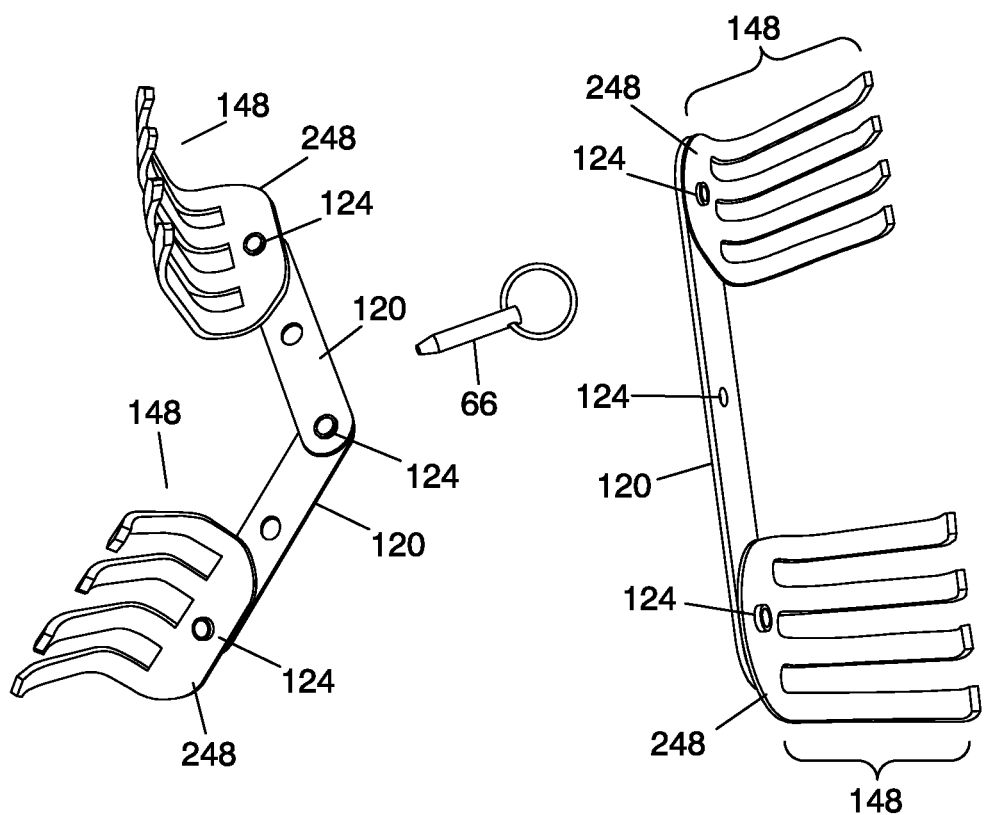

FIGS. 24A-24C show views of a sub-assembly 130 including a self-positioning arm 120, retractor blades 248 (showing finger extensions 148) and a quick connect fastener pin 66. Self-positioning arm 120 is rotatable about receiving well 124, where quick connect fastener pin 66 is shown. In this embodiment, the retractor blades 248 are aligned with the self-positioning arm 120 but in other embodiments, the retractor blades 248 may be connected to the self-positioning arm 120 via fasteners at receiving wells 124 that permit rotation about the self-positioning arm. The finger extensions 148 of retractor blades 248 may be selected to have any suitable number and to have any suitable length as described herein. In FIG. 24A, the self-positioning arm 120 is rotated to have an angle of less than 180 degrees between the two halves of the arm 120. In FIG. 24B the two halves of the self-positioning arm 120 are disposed at 180 degrees (flat) relative to each other. FIG. 24C shows perspective views of two sub-assemblies 130 of retractor blades 248, self-positioning arm 120 and quick connect fastener pin 66.

Described herein are retractor assemblies, which can provide numerous advantages for a user because of their lightweight design and wide range of maneuverability. Each of the locking mechanisms described herein allow fast and easy adjustment of the width of the retractor assembly 10. The slot(s) 30 provide(s) a lightweight design that increases the ease of handling and maneuvering the retractor assembly 10. The receiving wells 34 and the receiving slot 38 provide for numerous assemblies based on the desired use, and the quick connect design of the fasteners may provide easy and safe removal and addition of retractor blades 48. The angled design also provides a wider view of the incision and provides easier access and sightline without the hindrance of extra support bars across the retractor.

When a feature or element is herein referred to as being "on" another feature or element, it can be directly on the other feature or element or intervening features and/or elements may also be present. In contrast, when a feature or element is referred to as being "directly on" another feature or element, there are no intervening features or elements present. It will also be understood that, when a feature or element is referred to as being "connected", "attached" or "coupled" to another feature or element, it can be directly connected, attached or coupled to the other feature or element or intervening features or elements may be present. In contrast, when a feature or element is referred to as being "directly connected", "directly attached" or "directly coupled" to another feature or element, there are no intervening features or elements present. Although described or shown with respect to one embodiment, the features and elements so described or shown can apply to other embodiments. It will also be appreciated by those of skill in the art that references to a structure or feature that is disposed "adjacent" another feature may have portions that overlap or underlie the adjacent feature.

Terminology used herein is for the purpose of describing particular embodiments only and is not intended to be limiting of the invention. For example, as used herein, the singular forms "a", "an" and "the" are intended to include the plural forms as well, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof. As used herein, the term "and/or" includes any and all combinations of one or more of the associated listed items and may be abbreviated as "/".

Spatially relative terms, such as "under", "below", "lower", "over", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if a device in the figures is inverted, elements described as "under" or "beneath" other elements or features would then be oriented "over" the other elements or features. Thus, the exemplary term "under" can encompass both an orientation of over and under. The device may be otherwise oriented (rotated 90 degrees or at other orientations) and the spatially relative descriptors used herein interpreted accordingly. Similarly, the terms "upwardly", "downwardly", "vertical", "horizontal" and the like are used herein for the purpose of explanation only unless specifically indicated otherwise.

Although the terms "first" and "second" may be used herein to describe various features/elements (including steps), these features/elements should not be limited by these terms, unless the context indicates otherwise. These terms may be used to distinguish one feature/element from another feature/element. Thus, a first feature/element discussed below could be termed a second feature/element, and similarly, a second feature/element discussed below could be termed a first feature/element without departing from the teachings of the present invention.

Throughout this specification and the claims which follow, unless the context requires otherwise, the word "comprise", and variations such as "comprises" and "comprising" means various components can be co-jointly employed in the methods and articles (e.g., compositions and apparatuses including device and methods). For example, the term "comprising" will be understood to imply the inclusion of any stated elements or steps but not the exclusion of any other elements or steps.

In general, any of the apparatuses and methods described herein should be understood to be inclusive, but all or a sub-set of the components and/or steps may alternatively be exclusive, and may be expressed as "consisting of" or alternatively "consisting essentially of" the various components, steps, sub-components or sub-steps.

As used herein in the specification and claims, including as used in the examples and unless otherwise expressly specified, all numbers may be read as if prefaced by the word "about" or "approximately," even if the term does not expressly appear. The phrase "about" or "approximately"

may be used when describing magnitude and/or position to indicate that the value and/or position described is within a reasonable expected range of values and/or positions. For example, a numeric value may have a value that is +/−0.1% of the stated value (or range of values), +/−1% of the stated value (or range of values), +/−2% of the stated value (or range of values), +/−5% of the stated value (or range of values), +/−10% of the stated value (or range of values), etc. Any numerical values given herein should also be understood to include about or approximately that value, unless the context indicates otherwise. For example, if the value "10" is disclosed, then "about 10" is also disclosed. Any numerical range recited herein is intended to include all sub-ranges subsumed therein. It is also understood that when a value is disclosed that "less than or equal to" the value, "greater than or equal to the value" and possible ranges between values are also disclosed, as appropriately understood by the skilled artisan. For example, if the value "X" is disclosed the "less than or equal to X" as well as "greater than or equal to X" (e.g., where X is a numerical value) is also disclosed. It is also understood that the throughout the application, data is provided in a number of different formats, and that this data, represents endpoints and starting points, and ranges for any combination of the data points. For example, if a particular data point "10" and a particular data point "15" are disclosed, it is understood that greater than, greater than or equal to, less than, less than or equal to, and equal to 10 and 15 are considered disclosed as well as between 10 and 15. It is also understood that each unit between two particular units are also disclosed. For example, if 10 and 15 are disclosed, then 11, 12, 13, and 14 are also disclosed.

Although various illustrative embodiments are described above, any of a number of changes may be made to various embodiments without departing from the scope of the invention as described by the claims. For example, the order in which various described method steps are performed may often be changed in alternative embodiments, and in other alternative embodiments one or more method steps may be skipped altogether. Optional features of various device and system embodiments may be included in some embodiments and not in others. Therefore, the foregoing description is provided primarily for exemplary purposes and should not be interpreted to limit the scope of the invention as it is set forth in the claims.

The examples and illustrations included herein show, by way of illustration and not of limitation, specific embodiments in which the subject matter may be practiced. As mentioned, other embodiments may be utilized and derived there from, such that structural and logical substitutions and changes may be made without departing from the scope of this disclosure. Such embodiments of the inventive subject matter may be referred to herein individually or collectively by the term "invention" merely for convenience and without intending to voluntarily limit the scope of this application to any single invention or inventive concept, if more than one is, in fact, disclosed. Thus, although specific embodiments have been illustrated and described herein, any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

What is claimed is:

1. A method of retracting tissue, the method comprising:
positioning a C-shaped first arm of a retractor assembly against a first portion of a tissue, wherein the C-shaped first arm comprises a plurality of plates extending in parallel along a length of the C-shaped first arm;
positioning a C-shaped second arm of the retractor assembly against a second portion of the tissue, wherein the C-shaped second arm comprises a plurality of plates extending in parallel along a length of the C-shaped second arm; and
ratcheting the C-shaped first arm relative to the C-shaped second arm by pivoting the C-shaped first arm relative to the C-shaped second arm in a plane that is parallel to the plates forming the C-shaped first arm and engaging a ratcheting lock between the C-shaped first arm and the C-shaped second arm to prevent reduction of an angle between the C-shaped first arm and the C-shaped second arm until a release is activated, while allowing the angle to be increased,
wherein the plurality of plates extending in parallel along the length of the C-shaped first arm are each separated from each other by one or more spacing distances between 0.5 mm and 2 cm and the plurality of plates extending in parallel along the length of the C-shaped second arm are each separated from each other by one or more spacing distances between 0.5 mm and 2 cm.

2. The method of claim 1, further comprising inserting one or more tools at least partially into a space formed between a first c-shaped plate and a second C-shaped plate forming the C-shaped first arm.

3. The method of claim 1, further comprising releasing the ratcheting lock by releasing a first quick release plate disposed along the C-shaped first arm and a second quick release plate disposed along the C-shaped second arm.

4. The method of claim 3, wherein releasing the ratcheting lock comprises releasing engagement of the first quick release plate from a first set of ratchet teeth disposed on a first end of the C-shaped second arm.

5. The method of claim 3, wherein releasing the ratcheting lock comprises releasing engagement of the second quick release plate from a second set of ratchet teeth disposed on a first end of the C-shaped first arm.

6. The method of claim 3, wherein releasing the ratcheting lock comprises driving the first quick release plate against a bias and away from a set of ratchet teeth.

7. The method of claim 3, wherein releasing the first quick release plate comprises sliding the first quick release plate between the plates forming the C-shaped first arm.

8. The method of claim 1, further comprising engaging a tool in one or more receiving wells in the C-shaped first arm and/or the C-shaped second arm.

9. The method of claim 1, further comprises coupling a retractor blade to a distal end of the C-shaped first arm.

10. A method of retracting tissue, the method comprising:
positioning a C-shaped first arm of a retractor assembly against a first portion of a tissue, wherein the C-shaped first arm comprises a first plate and a second plate that are separated from each other by a first spacing distance and wherein the first plate and the second plate extend in parallel along a majority of a length of a C-shape of the C-shaped first arm;
positioning a C-shaped second arm of the retractor assembly against a second portion of the tissue, wherein the C-shaped second arm comprises a third plate and a fourth plate that are separated from each other by a second spacing distance, wherein the third plate and the fourth plate extend in parallel along a majority of a length of a C-shape of the C-shaped second arm, wherein the first and second spacing distances are between 0.5 mm and 2 cm; and ratcheting the C-shaped first arm relative to the C-shaped second arm by pivoting the C-shaped first arm relative to the C-shaped second arm in a plane that is parallel to the first plate, the second plate, the third plate and the fourth plate, and engaging a ratcheting lock to prevent reduction of an angle between the C-shaped first arm and the C-shaped second arm until a release is activated, while allowing the angle between the C-shaped first arm and the C-shaped second arm to be increased.

11. The method of claim 10, further comprising inserting one or more tools at least partially into a space formed between a first c-shaped plate and a second C-shaped plate forming the C-shaped first arm.

12. The method of claim 10, further comprising releasing the ratcheting lock by releasing a first quick release plate disposed along the C-shaped first arm and a second quick release plate disposed along the C-shaped second arm.

13. The method of claim 12, wherein releasing the ratcheting lock comprises releasing engagement of the first quick release plate from a first set of ratchet teeth disposed on a first end of the C-shaped second arm.

14. The method of claim 12, wherein releasing the ratcheting lock comprises releasing engagement of the second quick release plate from a second set of ratchet teeth disposed on a first end of the C-shaped first arm.

15. The method of claim 12, further wherein releasing the ratcheting lock comprises driving the first quick release plate against a bias and away from a set of ratchet teeth.

16. The method of claim 10, further comprising engaging a tool in one or more receiving wells in the C-shaped first arm and/or the C-shaped second arm.

17. The method of claim 10, wherein positioning the C-shaped first arm of the retractor assembly against the first portion of a tissue further comprises engaging a retractor blade at a distal end of the C-shaped first arm against the first portion of the tissue.

18. A method of retracting tissue, the method comprising:
positioning a C-shaped first arm of a retractor assembly against a first portion of a tissue, wherein the C-shaped first arm comprises a plurality of plates extending in parallel along a length of the C-shaped first arm;

positioning a C-shaped second arm of the retractor assembly against a second portion of the tissue, wherein the C-shaped second arm comprises a plurality of plates extending in parallel along a length of the C-shaped second arm;

ratcheting the C-shaped first arm relative to the C-shaped second arm by pivoting the C-shaped first arm relative to the C-shaped second arm in a plane that is parallel to the plates forming the C-shaped first arm and engaging a ratcheting lock between the C-shaped first arm and the C-shaped second arm to prevent reduction of an angle between the C-shaped first arm and the C-shaped second arm until a release is activated, while allowing the angle to be increased; and releasing the ratcheting lock by releasing a first quick release plate disposed along the C-shaped first arm and a second quick release plate disposed along the C-shaped second arm, wherein releasing the first quick release plate comprises sliding the first quick release plate between the plates forming the C-shaped first arm.

* * * * *